(12) United States Patent
Rothe et al.

(10) Patent No.: US 10,026,902 B2
(45) Date of Patent: Jul. 17, 2018

(54) SEMICONDUCTING MATERIAL COMPRISING A PHOSPHINE OXIDE MATRIX AND METAL SALT

(71) Applicant: Novaled GmbH, Dresden (DE)

(72) Inventors: Carsten Rothe, Dresden (DE); Mike Zöllner, Dresden (DE)

(73) Assignee: NOVALED GMBH, Dresden (DE)

( * ) Notice: Subject to any disclaimer, the term of this patent is extended or adjusted under 35 U.S.C. 154(b) by 13 days.

(21) Appl. No.: 15/023,569

(22) PCT Filed: Oct. 9, 2014

(86) PCT No.: PCT/EP2014/071659
§ 371 (c)(1),
(2) Date: Mar. 21, 2016

(87) PCT Pub. No.: WO2015/052284
PCT Pub. Date: Apr. 16, 2015

(65) Prior Publication Data
US 2016/0211455 A1    Jul. 21, 2016

(30) Foreign Application Priority Data
Oct. 9, 2013  (EP) .................................. 13187905

(51) Int. Cl.
H01L 51/00  (2006.01)
C07F 9/53   (2006.01)
C07F 9/58   (2006.01)
C07F 5/02   (2006.01)
H01L 51/50  (2006.01)

(52) U.S. Cl.
CPC .......... *H01L 51/0054* (2013.01); *C07F 5/025* (2013.01); *C07F 9/5325* (2013.01); *C07F 9/587* (2013.01); *H01L 51/0052* (2013.01); *H01L 51/0058* (2013.01); *H01L 51/0077* (2013.01);
(Continued)

(58) Field of Classification Search
None
See application file for complete search history.

(56) References Cited

U.S. PATENT DOCUMENTS

2014/0353649 A1* 12/2014 Dorok .................. H01L 51/005
                                                257/40
2015/0108449 A1    4/2015 Huang et al.

FOREIGN PATENT DOCUMENTS

JP    2002-063989 A      2/2002
JP    2002063989 A  *    2/2002
(Continued)

OTHER PUBLICATIONS

Machine-generated English-language Translation of the Description of JP 2002-063989 A.*
(Continued)

*Primary Examiner* — Vu A Nguyen
(74) *Attorney, Agent, or Firm* — Eversheds Sutherland (US) LLP

(57) ABSTRACT

The disclosure refers to a semiconducting material comprising a phosphorous-containing compound and at least one lithium complex. Also provided are electronic devices comprising a cathode, an anode, and the semiconducting material comprising a phosphorous-containing compound arranged between the cathode and the anode. Furthermore, a compound and an electronic device are disclosed.

15 Claims, 8 Drawing Sheets

(52) U.S. Cl.
CPC ...... *H01L 51/5072* (2013.01); *H01L 51/5092* (2013.01)

(56) References Cited

FOREIGN PATENT DOCUMENTS

| JP | 2004-204140 A | | 7/2004 | |
|----|---------------|---|--------|---|
| JP | 2004204140 A | * | 7/2004 | |
| JP | 2010-278376 A | | 12/2010 | |
| WO | 2013/079678 A1 | | 6/2013 | |
| WO | WO 2013079678 A1 | * | 6/2013 | ........... H01L 51/005 |

OTHER PUBLICATIONS

PCT International Search Report and Written Opinion for PCT/EP2014/071659 dated Nov. 12, 2014 (12 pages).
Hapke et al., "Use of the Diels-Alder Cycloaddition of Tetracyclone and Internal Aryl Acetylenes for the Synthesis of Functionalized Atropisomeric Biaryls," Eur. J. Org. Chem, 2010, 509-514.
Chinese Office Action for CN Application No. 201480055720.6 dated Feb. 27, 2018 (10 pages) (English translation).

* cited by examiner

SEMICONDUCTING MATERIAL COMPRISING A PHOSPHINE OXIDE MATRIX AND METAL SALT

CROSS REFERENCE TO RELATED APPLICATIONS

This application is a U.S. national stage application of PCT/EP2014/071659, filed Oct. 9, 2014, which claims priority to European Application No. 13187905.8, filed Oct. 9, 2013. The contents of these applications are hereby incorporated by reference.

The present invention concerns organic semiconducting material with improved electrical properties, compound suitable for this organic semiconducting material and electronic device utilizing the improved electrical properties of the inventive semiconducting material.

I. BACKGROUND OF THE INVENTION

Among the electronic devices comprising at least a part based on material provided by organic chemistry, organic light emitting diodes (OLEDs) have a prominent position. Since the demonstration of efficient OLEDs by Tang et al. in 1987 (C. W. Tang et al., Appl. Phys. Lett. 51 (12), 913 (1987)), OLEDs developed from promising candidates to high-end commercial displays. An OLED comprises a sequence of thin layers substantially made of organic materials. The layers typically have a thickness in the range of 1 nm to 5 μm. The layers are usually formed either by means of vacuum deposition or from a solution, for example by means of spin coating or jet printing.

OLEDs emit light after the injection of charge carriers in the form of electrons from the cathode and in form of holes from the anode into organic layers arranged in between. The charge carrier injection is effected on the basis of an applied external voltage, the subsequent formation of excitons in a light emitting zone and the radiative recombination of those excitons. At least one of the electrodes is transparent or semitransparent, in the majority of cases in the form of a transparent oxide, such as indium tin oxide (ITO), or a thin metal layer.

It is an objective of the invention to overcome the drawbacks of the prior art and to provide compounds which can be successfully embedded in electrically doped semiconducting materials for use in electronic devices. The inventive semiconducting materials shall afford devices with better characteristics, especially with low voltage and higher efficiency, more specifically, OLEDs with higher power efficiency.

II. SUMMARY OF THE INVENTION

The object is achieved by a semiconducting material comprising
i) a compound according to formula (I):

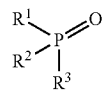

wherein $R^1$, $R^2$ and $R^3$ are independently selected from $C_1$-$C_{30}$-alkyl, $C_3$-$C_{30}$ cycloalkyl, $C_2$-$C_{30}$-heteroalkyl, $C_6$-$C_{30}$-aryl, $C_2$-$C_{30}$-heteroaryl, $C_1$-$C_{30}$-alkoxy, $C_3$-$C_{30}$-cycloalkyloxy, $C_6$-$C_{30}$-aryloxy, and from structural unit having general formula E-A-,
wherein A is a phenylene spacer unit and E is an electron transporting unit that is selected from $C_{10}$-$C_{60}$ aryl and $C_6$-$C_{60}$ heteroaryl comprising up to 6 heteroatoms independently selected from O, S, P, Si and B and that comprises a conjugated system of at least 10 delocalized electrons,
at least one group selected from $R^1$, $R^2$ and $R^3$ has the general formula E-A-, and
ii) at least one lithium complex having formula (II)

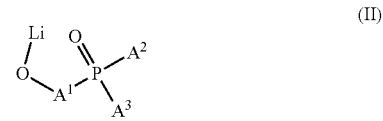

wherein $A^1$ is a $C_6$-$C_{30}$ arylene or $C_2$-$C_{30}$ heteroarylene comprising at least one atom selected from O, S and N in an aromatic ring and each of $A^2$-$A^3$ is independently selected from a $C_6$-$C_{30}$ aryl and $C_2$-$C_{30}$ heteroaryl comprising at least one atom selected from O, S and N in an aromatic ring.

The phenylene spacer A is preferably selected from ortho-, meta- and para-phenylene. For sterical reasons, m- and p-phenylene spacers are preferred.

The lithium complex (II) works in the inventive semiconducting material as an electrical dopant, whereas the compound of formula (I) has the function of a charge transporting matrix.

Examples of conjugated systems of delocalized electrons are systems of alternating pi- and sigma bonds, wherein, optionally, one or more two-atom structural units having the pi-bond between its atoms can be replaced by an atom bearing at least one lone electron pair, typically by a divalent O or S atom. Alternatively or in an addition, the system of alternating pi- and sigma bonds may embed one or more isolated boron atoms having only six valence electrons and one vacant orbital. Preferably, the conjugated system of delocalized electrons comprises at least one aromatic ring adhering to the Hickel rule. More preferably, the conjugated system of delocalized electrons comprises a condensed aromatic skeleton comprising at least 10 delocalized electrons, e.g. a naphthalene, anthracene, phenanthrene, pyrene, benzofurane or benzothiophene skeleton. Also preferably, the conjugated system of delocalized electrons may consist of at least two directly attached aromatic rings, the simplest examples of such systems being biphenyl, bithienyl, phenylthiophene, furylthiophene and like.

It is preferable that the lowest unoccupied molecular orbital (LUMO) of the compound (I) is localized mainly on its electron transporting units E. The presence of at least 10 delocalized electrons in the conjugated system makes the lowest unoccupied molecular orbital of the whole compound of formula (I) localized mainly on the electron transporting unit E.

More specifically, the localization of a frontier orbital like LUMO in the molecule can be assigned by a skilled person to that part of the molecule which contains the largest conjugated pi-electron system. In case that two or more pi-electron systems with the same extent (given by the number of pi electrons in conjugation) occur in the molecule, the lowest energy can be assigned to the system linked with strongest electron withdrawing groups and/or weakest electron donating groups. The electron withdrawing and/or electron accepting effects of various substituents are commensurate to experimentally accessible parameters like Hammet or Taft constants which are tabulated for large number of substituents most frequently occurring in aromatic or heteroaromatic organic compounds. In most cases, the above mentioned parameters are sufficient for a reliable LUMO localization, because the overall effect of more substituents attached to the same aromatic system is additive. In case of uncertainty, the ultimate method for the correct LUMO localization in the molecule is quantum chemical calculation. Reliable results with relatively low demand for computational capacity provide for example the methods based on density functional theory (DFT).

It is desirable that the LUMO level of compound (I), measured as a redox potential by cyclic voltammetry (CV) in tetrahydrofuran (THF) against ferrocenium/ferrocene redox couple as a reference, is in the range −1.8-−3.1 V. It is preferred that the energy of this LUMO is in the range −2.0-−2.9 V, more preferably in the range −2.15-−2.75 V, even more preferably in the range −2.25-−2.6 V. Modern quantum chemical methods allow also a reliable estimation of relative LUMO energies for different molecules. The computed relative values can be recalculated to absolute scale corresponding to the electrochemical potentials measured in a concrete CV experimental setting, if the calculated value is compared with the value measured for the same compound and the obtained difference is taken into account as a correction for the values calculated for other compounds.

Preferably, the semiconducting material comprising compounds of formula (I) and (II) serves as an electron transporting material or as an electron injecting material.

If not explicitly stated that a group or structural unit is unsubstituted, the given count of atoms (e.g., given count of carbon atoms) comprises also possible substituents.

Examples of an appropriate electron transporting unit are aryls and heteroaryls (arene or heteroarene radicals comprising at least two condensed aromatic rings). The term radical means an organic residue derived from an organic molecule by a formal hydrogen abstraction.

Even preferably, the electron transporting unit E is a $C_{14}$-$C_{50}$ aryl or heteroaryl. More preferably, the electron transporting unit E is a $C_{14}$-$C_{44}$ aryl.

Preferably, the electron transporting unit E comprises an aromatic or heteroaromatic skeleton having 2-5 condensed aromatic rings. More specifically, examples of the preferable electron transporting units are naphtyl, anthracenyl, phenanthrenyl, pyrenyl. 1,1'-biphenylyl is also preferable, although its rings are not condensed. Both the spacer A as well as the electron transporting unit E may be unsubstituted or appropriately substituted by electron withdrawing or electron donating groups which allow further tuning of the frontier orbital energy levels of the molecule. Typical examples of electron withdrawing groups are phenyl, halogen, carbonyl, nitrile, haloalkyl or haloaryl groups and six-membered nitrogen-containing heterocyclic radicals like pyridyl, diazinyl or triazinyl. Halogen means fluorine, chlorine, bromine or iodine; specific examples of haloalkyl and haloaryl groups are perhaloalkyl and perhaloaryl groups, like trichloromethyl, trifluoromethyl, pentafluoroethyl, heptafluoroisopropyl, perfluoro-tert-butyl or pentafluorophenyl. Examples of electron donating groups are alkyl groups like methyl, ethyl, propyl, isopropyl, heteroalkyl groups wherein one or more non-adjacent methylene units in the alkyl chain are replaced by a heteroatom, alkoxy groups, alkylthio groups, and five-membered heterocycles comprising up to three heteroatoms selected from N, O and S.

Typical examples of heteroatoms comprised in heteroalkyls are O, S and Si, represented by ether, sulphide or dialkylsilylene groups. Cycloalkyl has the meaning of a hydrocarbyl substituent which comprises at least one carbocyclic structure which is not aromatic. It is understood that the terms alkyl and cycloalkyl comprise also unsaturated and branched hydrocarbyl groups.

Any aryl, arylene, heteroaryl and/or heteroarylene in formula (II) may be independently unsubstituted or substituted with groups selected from alkoxy, aryloxy, lithiumoxy, and from hydrocarbon groups comprising only C and H, provided that the given C count in an aryl, heteroaryl, arylene or heteroarylene group includes also all substituents present on the said group.

Preferably, $A^1$ in formula (II) is phenylene. Also preferably, at least one of substituents $A^2$ and $A^3$ is phenyl.

It is preferred that the semiconducting material according to the invention comprises the salt (II) and a compound according to formula (I) at least partly in form of a homogeneous mixture, wherein both components are molecularly dispersed in each other.

Another object the invention is achieved by an electronic device comprising at least one semiconducting material according to the invention, preferably in form of an electronic device wherein the inventive semiconducting material forms at least one layer between a cathode and an anode.

Specifically, the second object of the invention is represented by an electronic device comprising at least one semiconducting layer comprising the semiconducting material according to the invention or consisting of it. More specifically, the semiconducting material according to the invention is used in the electronic device as an electron transporting layer, as an electron injecting layer, or as a layer having double electron transporting and hole blocking function.

In specific cases, also exciton blocking function can be considered.

Preferably, the arrangement of the inventive device does not allow that the inventive semiconducting layer emits light. In other words, it is preferred that only electrons enter the inventive semiconducting layer, whereas the access of holes is blocked, preventing thus exciton formation.

Another object of the invention is achieved by a compound having the structure according to formula (I)

wherein $R^1$, $R^2$ and $R^3$ are independently selected from $C_1$-$C_{30}$-alkyl, $C_3$-$C_{30}$-cycloalkyl, $C_2$-$C_{30}$-heteroalkyl, $C_6$-$C_{30}$-aryl, $C_2$-$C_{30}$-heteroaryl, $C_1$-$C_{30}$-alkoxy, $C_3$-$C_{30}$-cycloalkyloxy, $C_6$-$C_{30}$-aryloxy and from structural unit having general formula E-A-, and at least one group selected from $R^1$, $R^2$ and $R^3$ has the general formula E-A-, wherein A is phenylene and each E is an electron transporting unit that is independently selected from $C_{14}$-$C_{60}$-aryl and $C_6$-$C_{60}$ heteroaryl comprising up to 6 heteroatoms independently selected from O, S, P, Si and B and that comprises a conjugated system of at least 10 delocalized electrons, with the proviso that the compound (I), wherein $R^2$ and $R^3$ are both phenyl and in $R^1$, A is p-phenylene and E is $C_{14}$-$C_{38}$ anthryl, is excluded.

Preferably, the electron transporting unit -E is selected from $C_{14}$-$C_{50}$ aryl and $C_8$-$C_{50}$ heteroaryl, more preferably, -E is $C_{14}$-$C_{44}$ aryl. Even more preferably, -E is selected from $C_{16}$-$C_{44}$ pyrenyl and $C_4$-$C_{42}$ anthryl. Also preferably, in at least one electron transporting unit -E-A, i) A is m- or p-phenylene and E is $C_{16}$-$C_{44}$ pyrenyl or
ii) A is m-phenylene and E is $C_{14}$-$C_{38}$ anthryl.

Even more preferably, the anthryl is $C_{14}$-$C_{36}$ anthryl. Also preferably, at least one of substituents $R^1$, $R^2$ and $R^3$ is phenyl. Even more preferably, the anthryl is 9-anthryl.

III. BRIEF DESCRIPTION OF THE DRAWINGS

Figure 9:
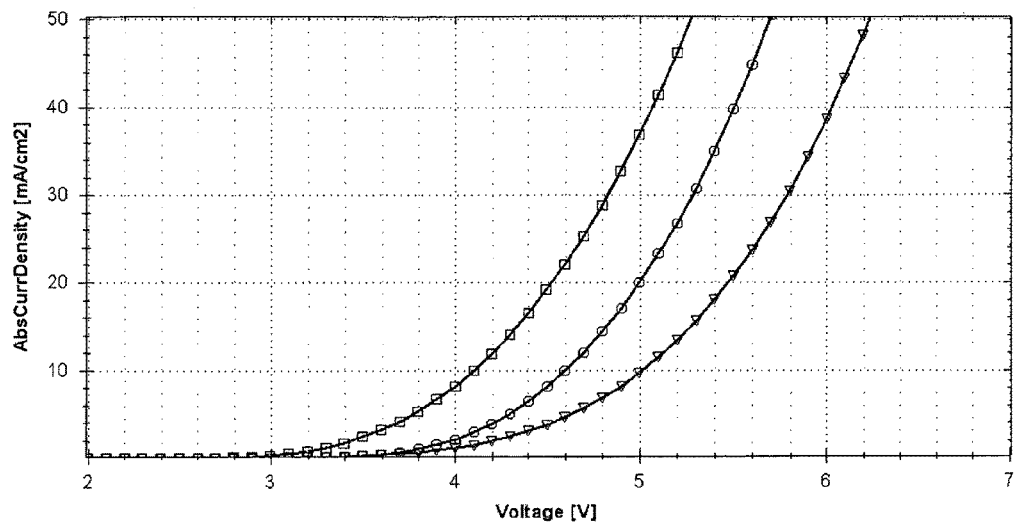

FIG. 9 compares the current density versus applied bias for the inventive semiconducting material B2+D2 (squares) and comparative materials C2+D2 (circles) and C2+D1 (triangles) in bottom emission OLEDs of example 1.

Figure 10:
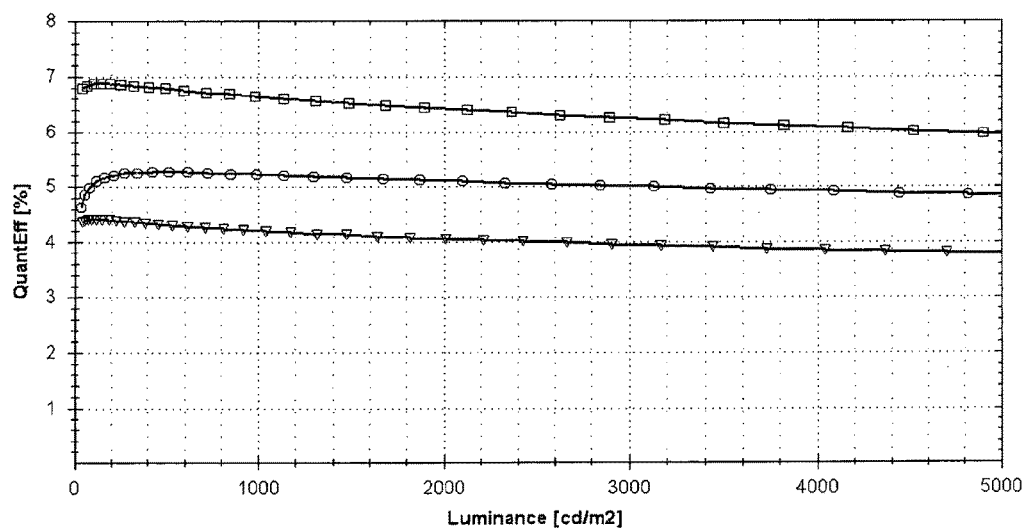

FIG. 10 compares the quantum efficiency versus luminance for the inventive semiconducting material B2+D2 (squares) and comparative materials C2+D2 (circles) and C2+D1 (triangles) in bottom emission OLEDs of example 1.

Figure 11:
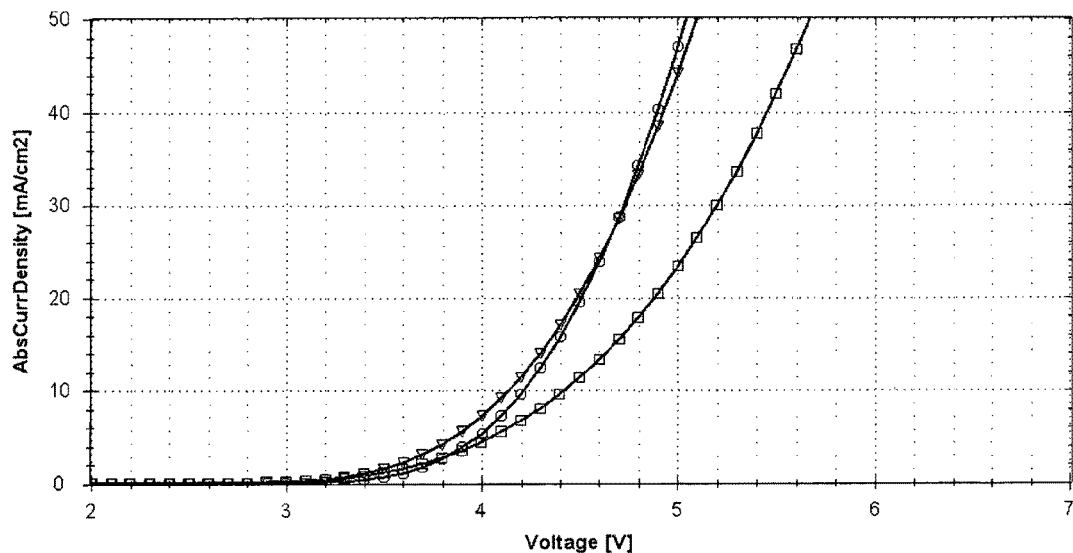

FIG. 11 compares the current density versus applied bias for the inventive semiconducting material A4+D2 (squares) and comparative materials C3+D2 (triangles) and C3+D1 (circles) in bottom emission OLEDs of example 1.

Figure 12:
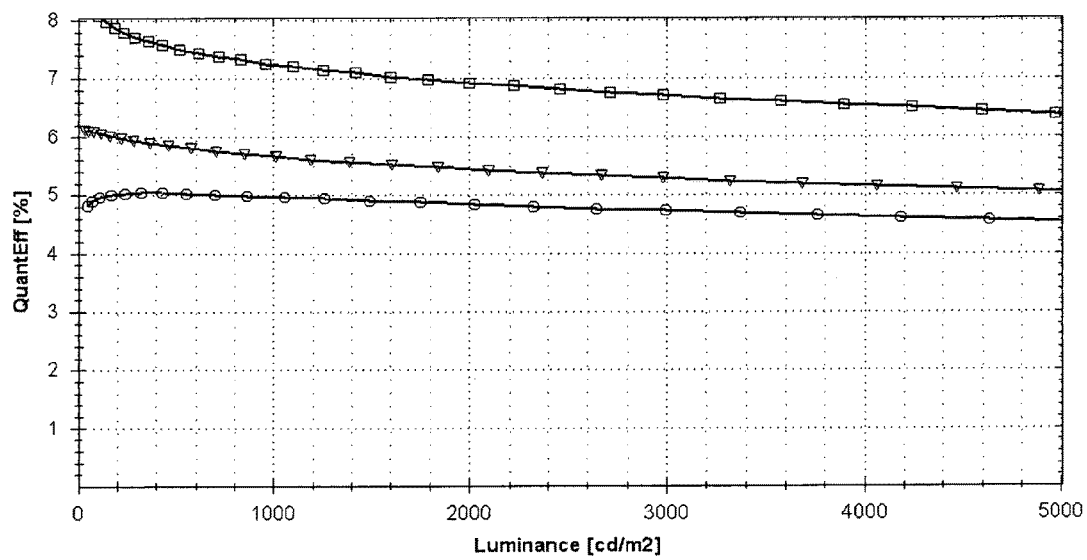

FIG. 12 compares the quantum efficiency versus luminance for the inventive semiconducting material A4+D2 (squares) and comparative materials C3+D2 (triangles) and C3+D1 (circles) in bottom emission OLEDs of example 1.

Figure 13:
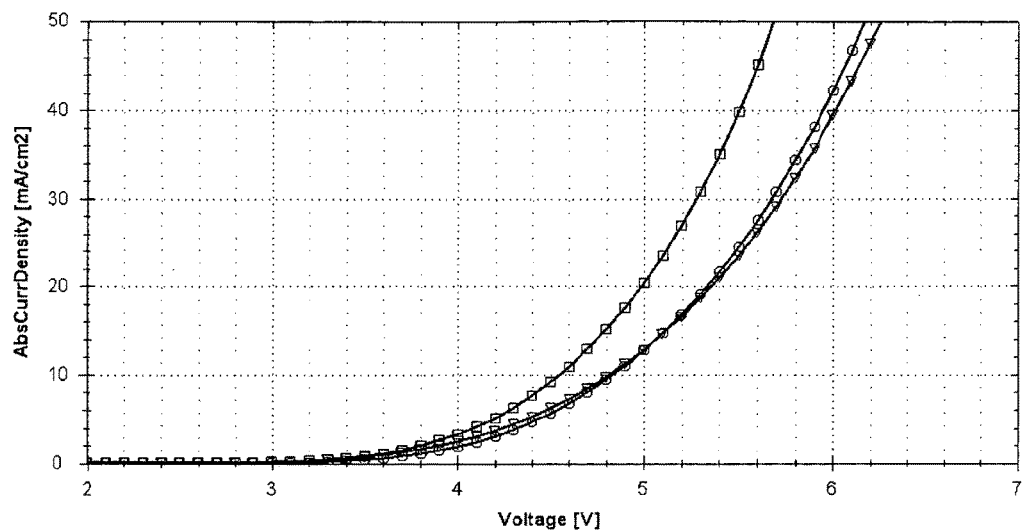

FIG. 13 compares the current density versus applied bias for the inventive semiconducting material A1+D2 (squares) and comparative materials C1+D2 (triangles) and C1+D1 (circles) in top emission OLEDs of example 2.

Figure 14:
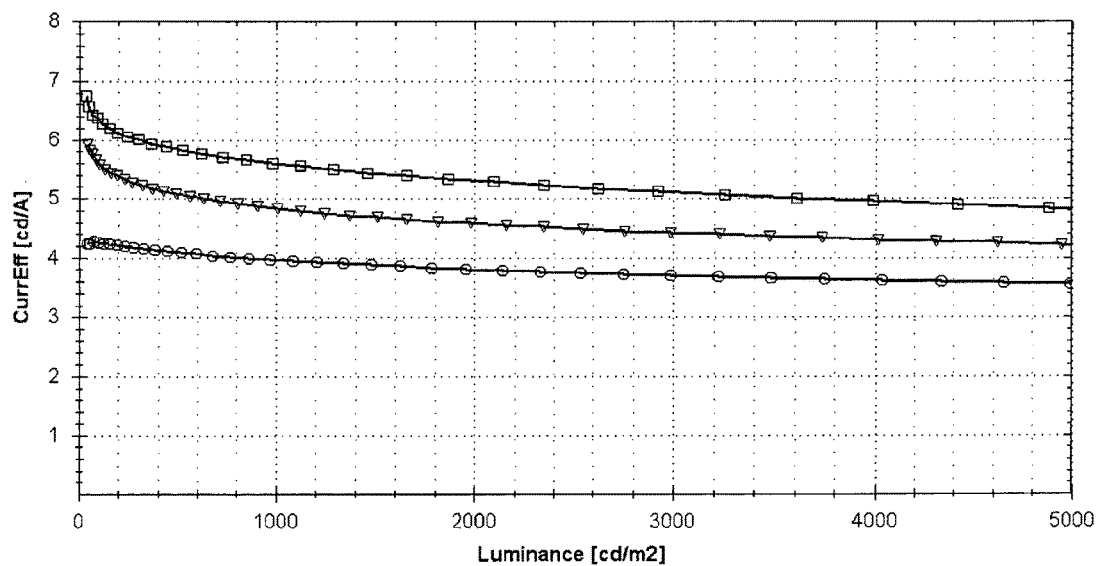

FIG. 14 compares the current efficiency versus luminance for the inventive semiconducting material A1+D2 (squares) and comparative materials C1+D2 (triangles) and C1+D1 (circles) in top emission OLEDs of example 2.

Figure 15:
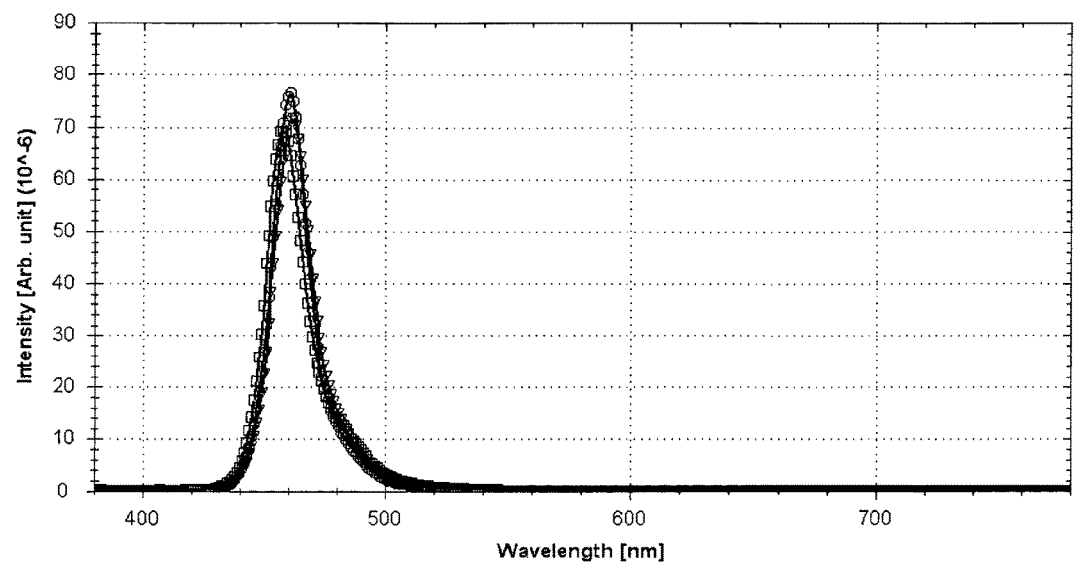

FIG. 15 compares spectral distribution of luminance for devices characterized on FIGS. 13-14 (squares: A1+D2, CIE y=0.050; circles: C1+D1, CIE y=0.045; triangles: C1+D2, CIE y=0.049).

IV. DETAILED DESCRIPTION OF THE INVENTION

Device Architecture

Figure 1:
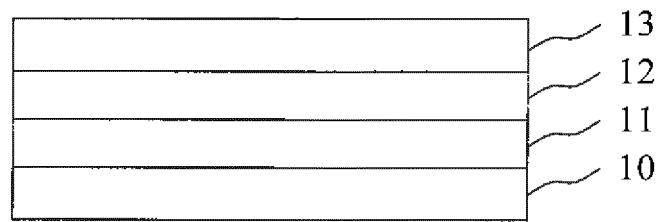
FIG. 1 shows a schematic illustration of a device in which the present invention can be incorporated.

FIG. 1 shows a stack of anode (10), organic semiconducting layer (11) comprising the light emitting layer (EML), electron transporting layer (ETL) (12), and cathode (13). Other layers can be inserted between those depicted, as explained herein.

Figure 2:
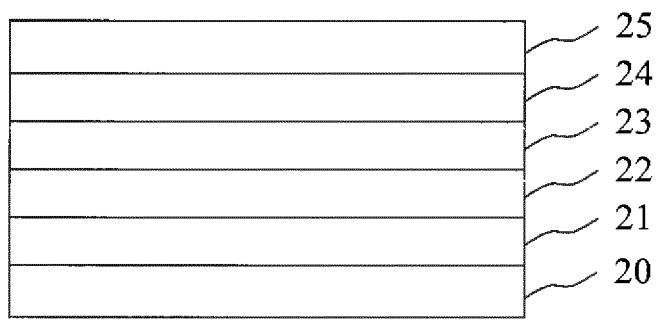
FIG. 2 shows a schematic illustration of a device in which the present invention can be incorporated.

FIG. 2 shows a stack of an anode (20), a hole injecting and transporting layer (21), a hole transporting layer (22) which can also aggregate the function of electron blocking, an EML (23), an ETL (24), and a cathode (25). Other layers can be inserted between those depicted, as explained herein.

The wording "device" comprises the organic light emitting diode.

Material Properties—Energy Levels

A method to determine the ionization potentials (IP) is the ultraviolet photoelectron spectroscopy (UPS). It is usual to measure the ionization potential for solid state materials; however, it is also possible to measure the IP in the gas phase. Both values are differentiated by their solid state effects, which are, for example the polarization energy of the holes that are created during the photo ionization process. A typical value for the polarization energy is approximately 1 eV, but larger discrepancies of the values can also occur. The IP is related to beginning of the photoemission spectra in the region of the large kinetic energy of the photoelectrons, i.e. the energy of the most weakly bounded electrons. A related method to UPS, the inverted photo electron spectroscopy (IPES) can be used to determine the electron affinity (EA). However, this method is less common. Electrochemical measurements in solution are an alternative to the determination of solid state oxidation ($E_{ox}$) and reduction ($E_{red}$) potential. An adequate method is for example the cyclo-voltammetry. A simple rule is used very often for the conversion of red/ox potentials into electron affinities and ionization potential: IP=4.8 eV+e*$E_{ox}$ (vs. ferrocenium/ferrocene (Fc$^+$/Fc)) and EA=4.8 eV+e*$E_{red}$ (vs. Fc$^+$/Fc) respectively (see B. W. D'Andrade, Org. Electron. 6, 11-20 (2005)). Processes are known for the correction of the electrochemical potentials in the case other reference electrodes or other redox pairs are used (see A. J. Bard, L. R. Faulkner, "Electrochemical Methods: Fundamentals and Applications", Wiley, 2. Ausgabe 2000). The information about the influence of the solution used can be found in N. G. Connelly et al., Chem. Rev. 96, 877 (1996). It is usual, even if not exactly correct to use the terms "energy of the HOMO" $E_{(HOMO)}$ and "energy of the LUMO" $E_{(LUMO)}$ respectively as synonyms for the ionization energy and electron affinity (Koopmans theorem). It has to be taken in consideration, that the ionization potentials and the electron affinities are given in such a way that a larger value represents a stronger binding of a released or respectively of an absorbed electron. The energy scale of the frontier molecular orbitals (HOMO, LUMO) is opposed to this. Therefore, in a rough approximation, is valid: IP=$-E_{(HOMO)}$ and EA=$E_{(LUMO)}$. The given potentials correspond to the solid-state potentials.

Substrate

It can be flexible or rigid, transparent, opaque, reflective, or translucent. The substrate should be transparent or translucent if the light generated by the OLED is to be transmitted through the substrate (bottom emitting). The substrate may be opaque if the light generated by the OLED is to be emitted in the direction opposite of the substrate, the so called top-emitting type. The OLED can also be transparent. The substrate can be either arranged adjacent to the cathode or anode.

Electrodes

The electrodes are the anode and the cathode, they must provide a certain amount of conductivity, being preferentially conductors. Preferentially the "first electrode" is the cathode. At least one of the electrodes must be semi-transparent or transparent to enable the light transmission to the outside of the device. Typical electrodes are layers or a stack of layer, comprising metal and/or transparent conductive oxide. Other possible electrodes are made of thin busbars (e.g. a thin metal grid) wherein the spaces between the busbars is filled (coated) with a transparent material with a certain conductivity, such as graphene, carbon nanotubes, doped organic semiconductors, etc.

In one mode, the anode is the electrode closest to the substrate, which is called non-inverted structure. In another mode, the cathode is the electrode closest to the substrate, which is called inverted structure.

Typical materials for the anode are ITO and Ag. Typical materials for the cathode are Mg:Ag (10 vol. % of Mg), Ag, ITO, Al. Mixtures and multilayer are also possible.

Preferably, the cathode comprises a metal selected from Ag, Al, Mg, Ba, Ca, Yb, In, Zn, Sn, Sm, Bi, Eu, Li, more preferably from Al, Mg, Ca, Ba and even more preferably selected from Al or Mg. Preferred is also a cathode comprising an alloy of Mg and Ag.

Hole-Transporting Layer (HTL)

Is a layer comprising a large gap semiconductor responsible to transport holes from the anode or holes from a CGL to the EML. The HTL is comprised between the anode and the EML or between the hole generating side of a CGL and the EML. The HTL can be mixed with another material, for example a p-dopant, in which case it is said the HTL is p-doped. The HTL can be comprised by several layers, which can have different compositions. P-doping the HTL lowers its resistivity and avoids the respective power loss due to the otherwise high resistivity of the undoped semiconductor. The doped HTL can also be used as optical spacer, because it can be made very thick, up to 1000 nm or more without significant increase in resistivity.

Suitable hole transport materials (HTM) can be, for instance HTM from the diamine class, where a conjugated system is provided at least between the two diamine nitrogens. Examples are N4,N4'-di(naphthalen-1-yl)-N4,N4'-diphenyl-[1,1'-biphenyl]-4,4'-diamine (HTM1), N4,N4,N4'',N4''-tetra([1,1'-biphenyl]-4-yl)-[1,1':4',1''-terphenyl]-4,4''-diamine (HTM2) or N4,N4''-di(naphthalen-1-yl)-N4,N4''-diphenyl-[1,1':4',1''-terphenyl]-4,4''-diamine (HTM3). The synthesis of diamines is well described in literature; many diamine HTMs are readily commercially available.

Hole-Injecting Layer (HIL)

Is a layer which facilitates the injection of holes from the anode or from the hole generating side of a CGL into an adjacent HTL. Typically the HIL is a very thin layer (<10 nm). The hole injection layer can be a pure layer of p-dopant and can be about 1 nm thick. When the HTL is doped, an HIL may not be necessary, since the injection function is already provided by the HTL.

Light-Emitting Layer (EML)

The light emitting layer must comprise at least one emission material and can optionally comprise additional layers. If the EML comprises a mixture of two or more materials the charge carrier injection can occur in different materials for instance in a material which is not the emitter, or the charge carrier injection can also occur directly into the emitter. Many different energy transfer processes can occur inside the EML or adjacent EMLs leading to different types of emission. For instance excitons can be formed in a host material and then be transferred as singlet or triplet excitons to an emitter material which can be singlet or triplet emitter which then emits light. A mixture of different types of emitter can be provided for higher efficiency. Mixed light can be realized by using emission from an emitter host and an emitter dopant.

Blocking layers can be used to improve the confinement of charge carriers in the EML, these blocking layers are further explained in U.S. Pat. No. 7,074,500 B2.

Electron-Transporting Layer (ETL)

Is a layer comprising a large gap semiconductor responsible to transport electrons from the cathode or electrons from a CGL or EIL (see below) to the EML. The ETL is comprised between the cathode and the EML or between the electron generating side of a CGL and the EML. The ETL can be mixed with an electrical n-dopant, in which case it is said the ETL is n-doped. The ETL can be comprised by several layers, which can have different compositions. Electrical n-doping the ETL lowers its resistivity and/or improves its ability to inject electrons into an adjacent layer and avoids the respective power loss due to the otherwise high resistivity (and/or bad injection ability) of the undoped semiconductor. The doped ETL can also be used as optical spacer, because it can be made very thick, up to 1000 nm or more without significant increase in resistivity.

The present invention also employs a compound according to formula (I) in the ETL, which compound can be used in combination with other materials, in the whole layer or in a sub-layer of the ETL.

Hole Blocking Layers and Electron Blocking Layers can be Employed as Usual.

In one mode of the invention the ETL comprises 2 layers, the first ETL (ETL1) and the second ETL (ETL2), ETL1 is closer to the EML than the ETL2. Preferentially ETL1 comprises the compound according to formula 1, even more preferably consists only of material according to formula (I). Also preferably, ETL1 is closer to the substrate than ETL2.

Alternatively or in addition, the ETL2 comprises a compound according to formula (I). Preferably, the ETL2 is electrically doped.

Optionally ETL1 and ETL2 comprise the same compound according to formula (I).

Other layers with different functions can be included, and the device architecture can be adapted as known by the skilled in the art. For example, an Electron-Injecting Layer (EIL) can be used between the cathode and the ETL. Also the EIL can comprise the inventive matrix compounds of the present application.

Charge Generation Layer (CGL)

The OLED can comprise a CGL which can be used in conjunction with an electrode as inversion contact, or as connecting unit in stacked OLEDs. A CGL can have the most different configurations and names, examples are pn-junction, connecting unit, tunnel junction, etc. Best examples are pn junctions as disclosed in US 2009/0045728 A1, US 2010/0288362 A1. Metal layers and or insulating layers can also be used.

Stacked OLEDs

When the OLED comprises two or more EMLs separated by CGLs, the OLED is named a stacked OLED, otherwise it is named a single unit OLED. The group of layers between two closest CGLs or between one of the electrodes and the closest CGL is named a electroluminescent unit (ELU). Therefore a stacked OLED can be described as anode/$ELU_1$/$\{CGL_X/ELU_{1+X}\}_X$/cathode, wherein x is a positive integer and each $CGL_X$ or each $ELU_{1+X}$ can be equal or different. The CGL can also be formed by the adjacent layers of two ELUs as disclosed in US2009/0009072 A1. Further stacked OLEDs are explained e.g. in US 2009/0045728 A1, US 2010/0288362 A1, and references therein.

Deposition of Organic Layers

Any organic semiconducting layers of the inventive display can be deposited by known techniques, such as vacuum thermal evaporation (VTE), organic vapour phase deposition, laser induced thermal transfer, spin coating, blade coating, slot dye coating, inkjet printing, etc. A preferred method for preparing the OLED according to the invention is vacuum thermal evaporation.

Preferably, the ETL is formed by evaporation. When using an additional material in the ETL, it is preferred that the ETL is formed by co-evaporation of the electron transporting matrix (ETM) and the additional material. The additional material may be mixed homogeneously in the ETL. In one mode of the invention, the additional material has a concentration variation in the ETL, wherein the concentration changes in the direction of the thickness of the stack of layers. It is also foreseen that the ETL is structured in sub-layers, wherein some but not all of these sub-layers comprise the additional material.

Electrical Doping

The present invention can be used in addition or in combination with electrical doping of organic semiconducting layers.

The most reliable and at the same time efficient OLEDs are OLEDs comprising electrically doped layers. Generally, the electrical doping means improving of electrical properties, especially the conductivity and/or injection ability of a doped layer in comparison with neat charge-transporting matrix without a dopant. In the narrower sense, which is usually called redox doping or charge transfer doping, hole transport layers are doped with a suitable acceptor material (p-doping) or electron transport layers with a donor material (n-doping), respectively. Through redox doping, the density of charge carriers in organic solids (and therefore the conductivity) can be increased substantially. In other words, the redox doping increases the density of charge carriers of a semiconducting matrix in comparison with the charge carrier density of the undoped matrix. The use of doped charge-carrier transport layers (p-doping of the hole transport layer by admixture of acceptor-like molecules, n-doping of the electron transport layer by admixture of donor-like molecules) in organic light-emitting diodes is, e.g., described in US 2008/203406 and U.S. Pat. No. 5,093,698.

US2008227979 discloses in detail the charge-transfer doping of organic transport materials, with inorganic and with organic dopants. Basically, an effective electron transfer occurs from the dopant to the matrix increasing the Fermi level of the matrix. For an efficient transfer in a p-doping case, the LUMO energy level of the dopant is preferably more negative than the HOMO energy level of the matrix or at least slightly more positive, not more than 0.5 eV, to the HOMO energy level of the matrix. For the n-doping case, the HOMO energy level of the dopant is preferably more positive than the LUMO energy level of the matrix or at least slightly more negative, not lower than 0.5 eV, to the LUMO energy level of the matrix. It is further more desired that the energy level difference for energy transfer from dopant to matrix is smaller than +0.3 eV.

Typical examples of known redox doped hole transport materials are: copperphthalocyanine (CuPc), which HOMO level is approximately −5.2 eV, doped with tetrafluoro-tetracyanoquinonedimethane (F4TCNQ), which LUMO level is about −5.2 eV; zincphthalocyanine (ZnPc) (HOMO=−5.2 eV) doped with F4TCNQ; a-NPD (N,N'-Bis(naphthalen-1-yl)-N,N'-bis(phenyl)-benzidine) doped with F4TCNQ. a-NPD doped with 2,2'-(perfluoronaphthalene-2,6-diylidene) dimalononitrile (PD1). a-NPD doped with 2,2', 2"-(cyclopropane-1,2,3-triylidene)tris(2-(p-cyanotetrafluorophenyl)acetonitrile) (PD2). All p-doping in the device examples of the present application was done with 8 wt. % PD2.

Typical examples of known redox doped electron transport materials are: fullerene C60 doped with acridine orange base (AOB); perylene-3,4,9,10-tetracarboxylic-3,4,9,10-di-anhydride (PTCDA) doped with leuco crystal violet; 2,9-di(phenanthren-9-yl)-4,7-diphenyl-1,10-phenanthroline doped with tetrakis (1,3,4,6,7,8-hexahydro-2H-pyrimido[1,2-a]pyrimidinato) ditungsten(II) (W$_2$(hpp)$_4$); naphthalene tetracarboxylic acid di-anhydride (NTCDA) doped with 3,6-bis-(dimethyl amino)-acridine; NTCDA doped with bis (ethylene-dithio) tetrathiafulvalene (BEDT-TTF).

In the present invention, classical redox dopants with high reduction strength, expressed as a highly negative redox potential measured by cyclic voltammetry (CV) in THF vs. Fc+/Fc standard, are successfully replaced with metal salts having no pronounced reductive properties. True mechanism how these compounds, sometimes called "electrically doping additives", contribute to the lowering of the voltage in electronic devices, is not yet known.

Typical known representative of such metal salts is lithium 8-hydroxyquinolinolate (LiQ) represented by the formula D1

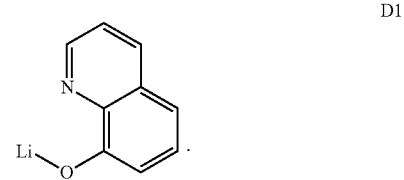

D1

Many other similar lithium complexes comprising five- or six-membered chelate ring wherein Li is coordinated to an oxygen and a nitrogen atom are known and were used or proposed as electrical dopants for organic electron transporting semiconducting materials.

As already stated above, the doped semiconducting material according to present invention comprises lithium salt having general formula (II)

Formula (II)

wherein $A^1$ is a $C_6$-$C_{30}$ arylene or $C_2$-$C_{30}$ heteroarylene comprising at least one atom selected from O, S and N in an aromatic ring and each of $A^2$-$A^3$ is independently selected from a $C_6$-$C_{30}$ aryl and $C_2$-$C_{30}$ heteroaryl comprising at least one atom selected from O, S and N in an aromatic ring, wherein any aryl, arylene, heteroaryl and/or heteroarylene may be independently unsubstituted or substituted with groups selected from hydrocarbon groups comprising only C and H, alkoxy, aryloxy and lithiumoxy, provided that the given C count in an aryl, heteroaryl, arylene or heteroarylene group includes also all substituents present on the said group.

It is to be understood that the term substituted or unsubstituted arylene stands for a divalent radical derived from substituted or unsubstituted arene, wherein the both adjacent structural moieties (in formula (II), the OLi group and the diaryl prosphine oxide group) are attached directly to an aromatic ring of the arylene group. Similarly, the term substituted or unsubstituted heteroarylene stands for a divalent radical derived from substituted or unsubstituted heteroarene, wherein the both adjacent structural moieties (in formula (II), the OLi group and the diaryl prosphine oxide group) are attached directly to an aromatic ring of the heteroarylene group. In examples of the present application, this class of dopants is represented by compounds D2 and D3

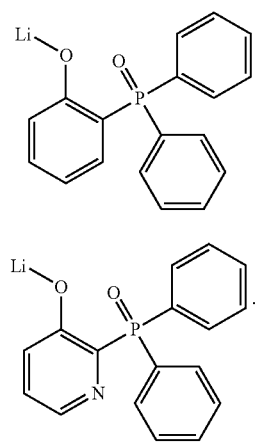

D2

D3

Compound D2 was disclosed in the application PCT/EP2012/074127, published as WO2013/079678 A1, and compound D3 in the application EP13170862.

Preferred ETL matrix compounds of the present invention are

A1

A2

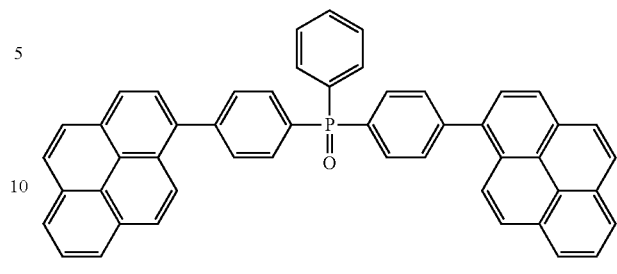

A3

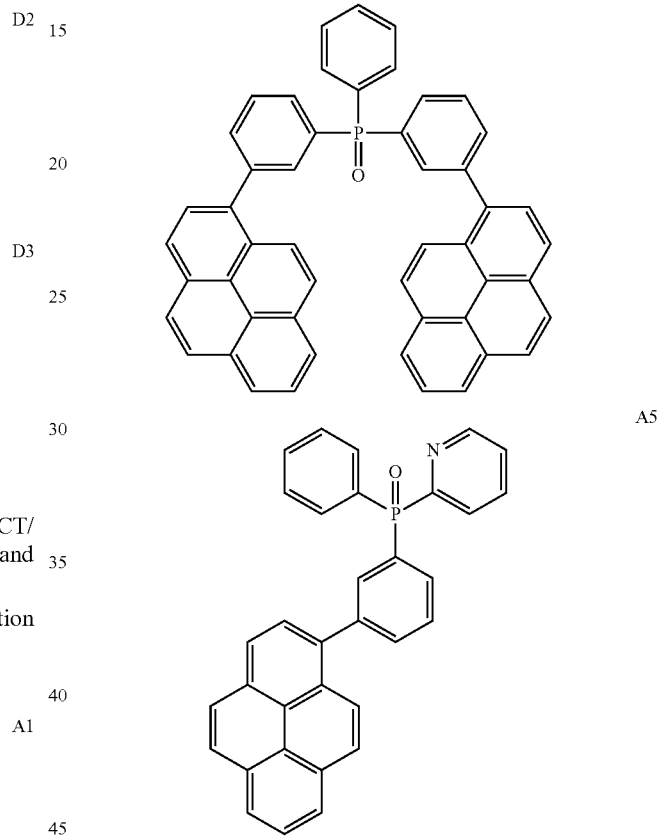

A4

A5

A6

A7
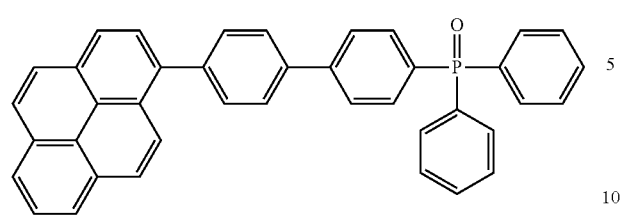
B1
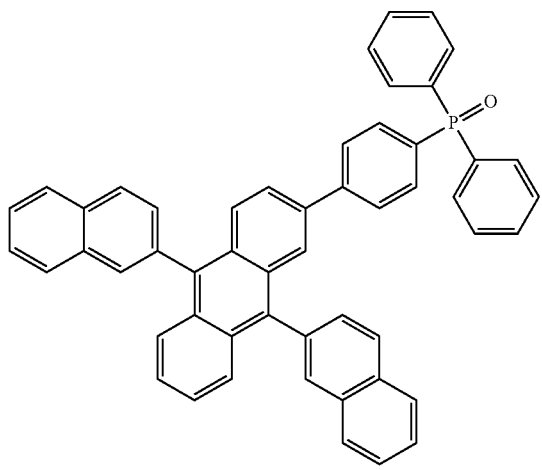
B2
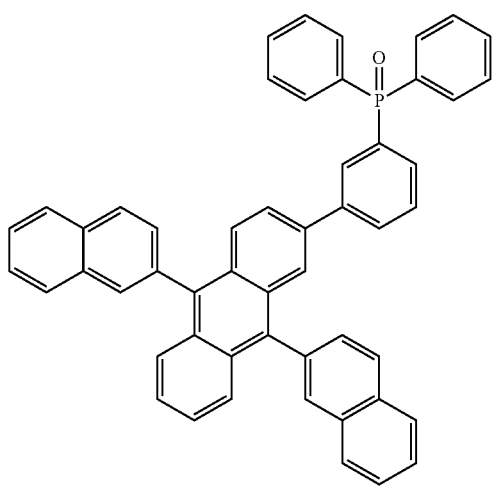
B3
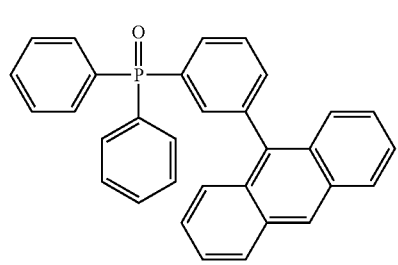
B4
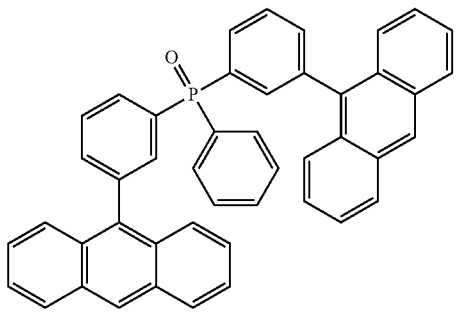
B5
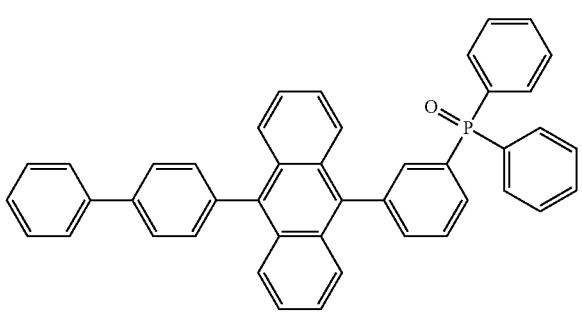
B6
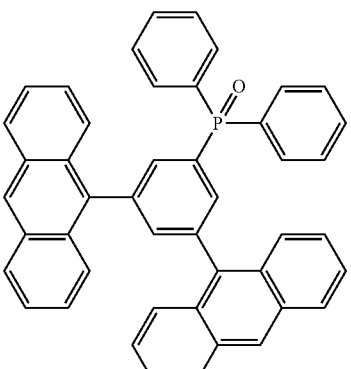
B7
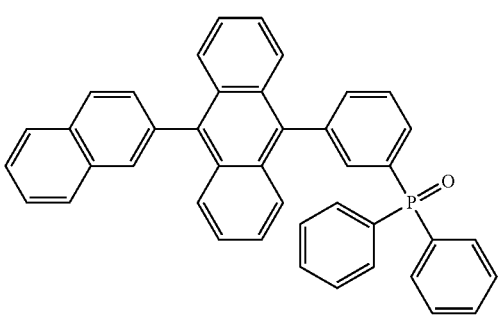

-continued

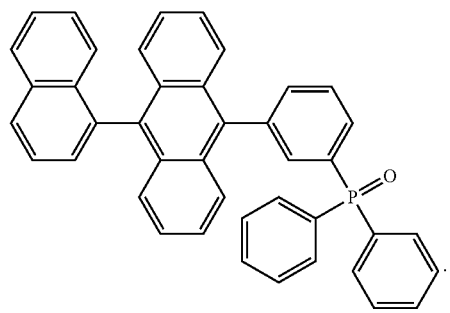
B8

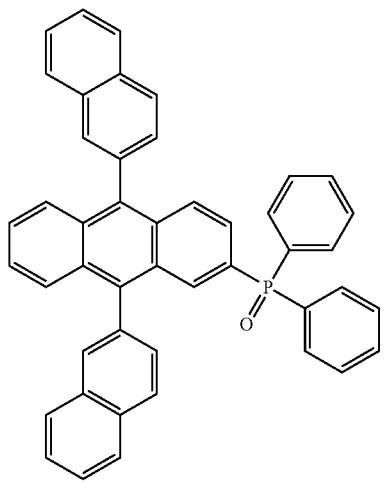
C2

V. ADVANTAGEOUS EFFECT OF THE INVENTION

The favourable effects of the inventive electron-transporting matrix materials are shown in comparison with comparative devices comprising instead of the inventive compounds electron transporting matrices which lack the inventive combination of phosphine oxide group and electron transporting unit with a phenylene spacer. Following comparative compounds are referred to:

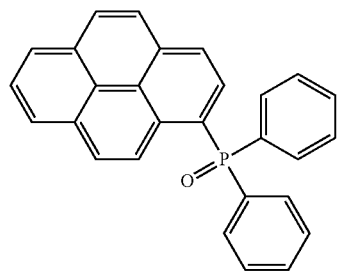
C1

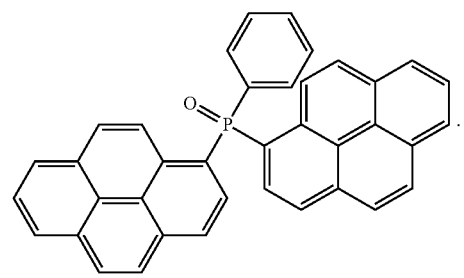
C3

Table 1 shows the performance of inventive and comparative compounds in bottom emission structured OLEDs, described in detail in example 1, with respect to voltage (U) and quantum efficiency (Qeff). Additionally the quotient Qeff/U (power efficiency) is taken as basis for enabling proper comparison in order to consider tradeoff effects between both values. The LUMO energies are represented by reversible electrochemical redox potentials of the studied compounds, measured by CV in THF against $Fc^+/Fc$ reference redox system.

TABLE 1

| Code | LUMO (V) | D1 doped | | | D2 doped | | | D3 doped | | |
|---|---|---|---|---|---|---|---|---|---|---|
| | | U (V) | Qeff | Q/U | U (V) | Qeff | Q/U | U (V) | Qeff | Q/U |
| A1 | −2.43 | 4.9 | 4.5 | 0.92 | 4.9 | 6.1 | 1.24 | | | |
| A2 | −2.47 | 5.2 | 5.4 | 1.04 | 5.1 | 6.7 | 1.31 | | | |
| A3 | −2.43 | 5.1 | 3.5 | 0.69 | 4.4 | 6.0 | 1.36 | | | |
| A4 | −2.48 | 4.7 | 5.9 | 1.26 | 4.4 | 7.4 | 1.68 | 4.2 | 8.2 | 1.95 |
| B1 | −2.27 | 4.3 | 5.0 | 1.16 | 4.3 | 5.9 | 1.37 | | | |
| B2 | −2.38 | 4.5 | 6.2 | 1.37 | 4.1 | 6.7 | 1.64 | | | |
| B3 | −2.42 | 5.2 | 4.3 | 0.83 | 5.1 | 5.6 | 1.10 | 5.1 | 6.2 | 1.22 |
| B4 | −2.43 | 4.4 | 5.5 | 1.25 | 4.2 | 6.8 | 1.62 | 3.9 | 8.3 | 2.13 |
| C2 | −2.19 | 4.6 | 5.2 | 1.13 | 5.0 | 4.4 | 0.88 | | | |
| C3 | −2.24 | 4.2 | 5.1 | 1.21 | 4.1 | 5.8 | 1.41 | | | |

Table 2 shows the performance of inventive compound A1 and the comparative compound (C1) in top emission structured OLEDs, described in detail in example 2, with respect to voltage (U) and current efficiency (Ceff). Additionally the quotient Ceff/U (power efficiency) is taken as basis for enabling proper comparison in order to consider tradeoff-effects between both values.

TABLE 2

| Code | LUMO (V) | D1 doped | | | D2 doped | | |
|---|---|---|---|---|---|---|---|
| | | U (V) | Ceff | C/U | U (V) | Ceff | C/U |
| A1 | −2.43 | 5.1 | 4.7 | 0.92 | 4.6 | 5.8 | 1.26 |
| C1 | −2.27 | 4.8 | 4.0 | 0.83 | 4.8 | 4.8 | 1.00 |

I. Examples

General Remarks for Synthesis

All reactions were carried out under argon atmosphere using oven dried glassware. Starting materials were used as purchased without further purification. Materials, which were used to build OLEDs, were sublimed by gradient sublimation to achieve highest purity.

General Procedure A: Triphenylphosphinoxide Synthesis

The halogen compound was dissolved in THF. 2.5M n-BuLi solution in hexane was slowly dropped to this solution chilled to −80° C. (temperature measured directly in the solution). The stirring was continued for one hour. Diphenyl phosphine chloride or phenylphosphine dichloride, respectively, was added slowly at −80° C. The reaction mixture was allowed to warm to room temperature (RT) and stirred overnight. After methanol addition and reduction to dryness, the residue was dissolved in dichloromethane (DCM). The organic phase was washed with water, dried over $Na_2SO_4$ and reduced to dryness.

The residue was dissolved in DCM again and oxidized with 30 wt. % aqueous hydrogen peroxide solution. After stirring overnight, the organic solution was washed with water, dried over $Na_2SO_4$ and reduced to dryness. The crude product was purified by column chromatography.

General Procedure B: Suzuki Coupling

The halogen compound, the boronic acid, $Pd(P^tBu_3)_4$ and the solvent were mixed together. A degassed 2M aqueous $K_2CO_3$ solution was added. The mixture was stirred at 85° C. (oil bath temperature) for 18 h and cooled afterwards. In case that a solid precipitated, the solid was filtered off and purified by column chromatography directly. Otherwise, the organic phase was washed with water, dried over $Na_2SO_4$, reduced to dryness and purified by column chromatography afterwards.

Analytics

Final materials were characterized by mass spectrometry (MS) and proton magnetic resonance ($^1H$-NMR). NMR samples were dissolved in $CD_2Cl_2$ unless otherwise stated. Melting points (mp) were determined by differential scanning calorimetry (DSC). Peak temperatures are reported. If gas chromatography-mass spectrometry (GC-MS) or high performance liquid chromatography (HPLC) with electrospray ionization mass spectroscopy (ESI-MS) were used for the product characterization, only the mass/charge (m/z) ratios for the molecular peak are reported. For brominated intermediates, the corresponding isotopic multiplet is reported.

(4-bromophenyl)diphenylphosphine oxide

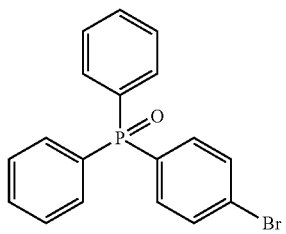 [SMILES: O=P(c1ccccc1)(c1ccccc1)c1ccc(Br)cc1]

According to general procedure A)
1,4-dibromobenzene: 10.00 g (42.4 mmol, 1.0 eq)
n-butyllithium, 2.5M in hexane: 17 mL (42.4 mmol, 1.0 eq)
chlorodiphenylphosphine: 9.35 g (42.4 mmol, 1.0 eq)
THF: 50 mL
DCM: 50 mL
$H_2O_2$, 30 wt. % in water: 10 mL
Column chromatography: $SiO_2$, ethyl acetate
Yield: 6.84 g white solid (45% theoretical)
mp: 166° C.
GC-MS: m/z=356, 358 bis(4-bromophenyl)(phenyl)phosphine oxide

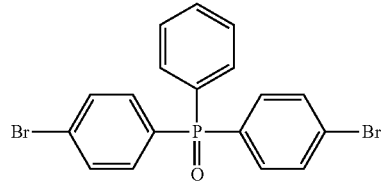 [SMILES: O=P(c1ccccc1)(c1ccc(Br)cc1)c1ccc(Br)cc1]

According to general procedure A
1,4-dibromobenzene: 10.00 g (42.4 mmol, 1.0 eq)
n-butyl lithium, 2.5M in hexane: 17 mL (42.4 mmol, 1.0 eq)
dichlorophenylphosphine: 3.79 g (21.2 mmol, 0.5 eq), dissolved in 50 mL THF
THF: 100 mL
DCM: 50 mL
$H_2O_2$, 30 wt. % in water: 10 mL
Column chromatography: $SiO_2$, ethyl acetate
Yield: 5.0 g viscous oil (54%)
mp: 125° C.
GC-MS: m/z=433, 435, 437

(3-bromophenyl)diphenylphosphine oxide

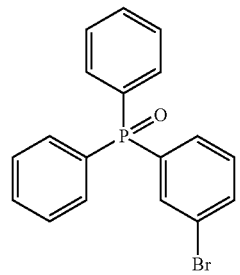 [SMILES: O=P(c1ccccc1)(c1ccccc1)c1cccc(Br)c1]

According to general procedure A
1,3-dibromobenzene: 10.00 g (42.4 mmol, 1.0 eq)
n-butyl lithium, 2.5M in hexane: 17 mL (42.4 mmol, 1.0 eq)
chlorodiphenylphosphine: 9.35 g (42.4 mmol, 1.0 eq)
THF: 50 mL
DCM: 50 mL
$H_2O_2$, 30 wt. % in water: 10 mL
Column chromatography: $SiO_2$, ethyl acetate, $R_f$=0.52
Yield: 9.6 g white solid (63%)
mp: 95° C.
GC-MS: m/z=356, 358 bis(3-bromophenyl) (phenyl)phosphine oxide

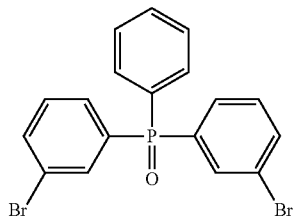 [SMILES: O=P(c1ccccc1)(c1cccc(Br)c1)c1cccc(Br)c1]

According to general procedure A
1,3-dibromobenzene: 10.00 g (42.4 mmol, 1.0 eq)
n-butyllithium, 2.5M in hexane: 17 mL (42.4 mmol, 1.0 eq)
dichlorophenylphosphine: 3.58 g (21.2 mmol, 0.5 eq), dissolved in 50 mL THF
THF: 100 mL
DCM: 50 mL
$H_2O_2$, 30 wt. % in water: 10 mL
Column chromatography: $SiO_2$, ethyl acetate
Yield: 6.86 g (74%) white solid
mp: 103° C.
GC-MS: m/z=434, 436, 438 diphenyl(4-(pyren-1-yl)phenyl)phosphine oxide
(A1)

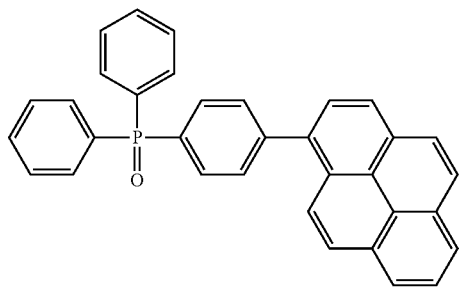 [SMILES: O=P(c1ccccc1)(c1ccccc1)c1ccc(-c2ccc3ccc4cccc5ccc2c3c45)cc1]

Figure 3:
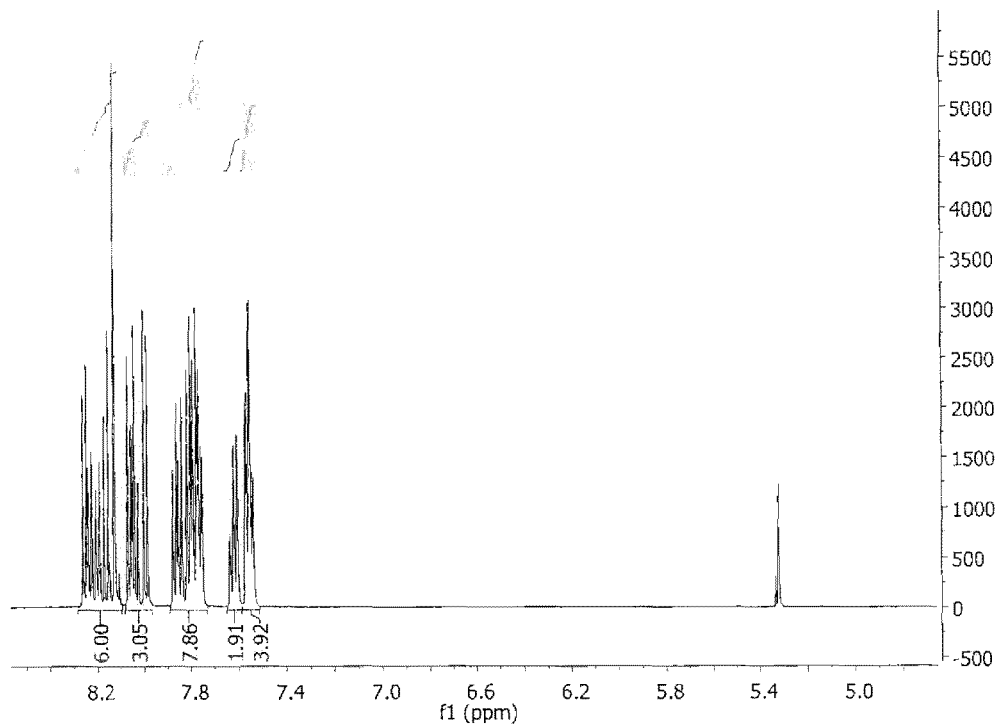
FIG. 3 shows $^1$H NMR spectrum of the inventive compound A1

According to general procedure B
(4-bromophenyl)diphenylphosphine oxide: 4.8 g (13.4 mmol, 1.0 eq)
1-pyreneboronic acid: 3.97 g (16.1 mmol, 1.2 eq)
Pd(PPh$_3$)$_4$: 466 mg (0.40 mmol, 3 mol. %)
K$_2$CO$_3$, 2M: 20 mL
1,2-dimethoxyethane (DME): 60 mL
Column chromatography: $SiO_2$, ethyl acetate
Yield: 4.45 g (69%) pale yellow solid mp: 208° C.
EI-MS: m/z=478
$^1$H-NMR: see FIG. 3 diphenyl(3-(pyren-1-yl)phenyl)phosphine oxide
(A2)

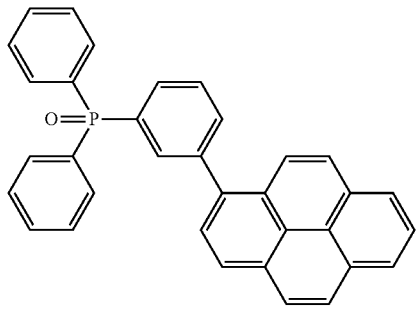 [SMILES: O=P(c1ccccc1)(c1ccccc1)c1cccc(-c2ccc3ccc4cccc5ccc2c3c45)c1]

Figure 4:
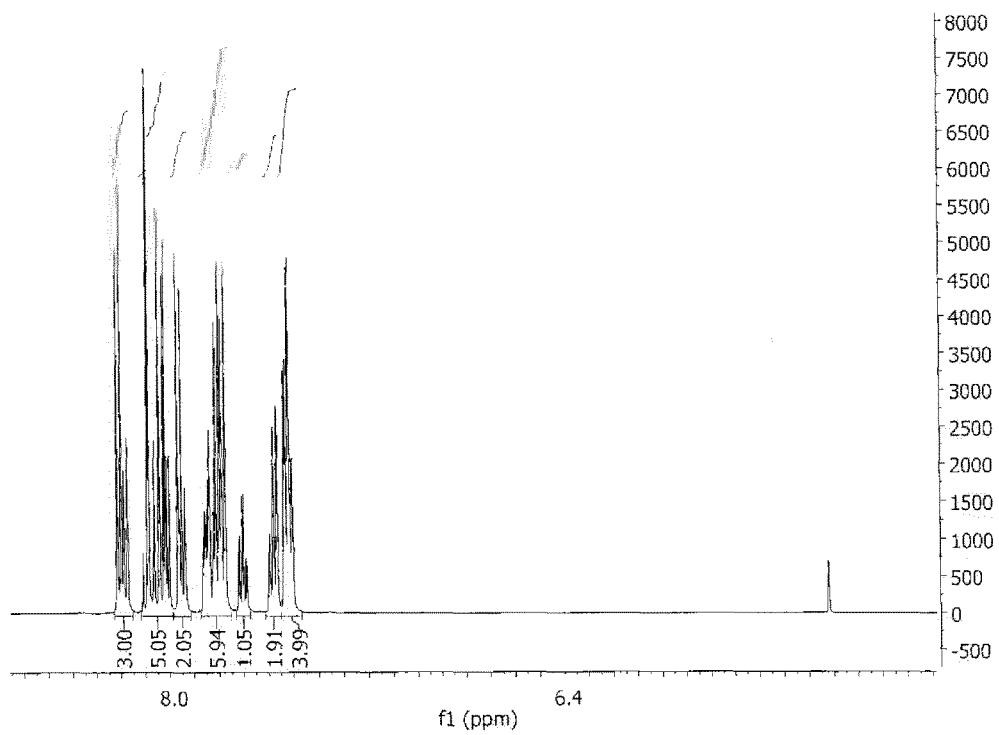
FIG. 4 shows $^1$H NMR spectrum of the inventive compound A2

According to general procedure B
(3-bromophenyl)diphenylphosphine oxide: 8.27 g (23.2 mmol, 1.0 eq)
1-pyreneboronic acid: 6.84 g (27.8 mmol, 1.2 eq)
Pd(PPh$_3$)$_4$: 803 mg (0.67 mmol, 3 mol. %)
K$_2$CO$_3$, 2M: 35 mL
DME: 100 mL
Column chromatography: $SiO_2$, ethyl acetate
Yield: 7.5 g yellow solid (68%)
mp: 198° C.
EI-MS: m/z=478
$^1$H-NMR: see FIG. 4 phenylbis(4-(pyren-1-yl)phenyl)phosphine oxide
(A3)

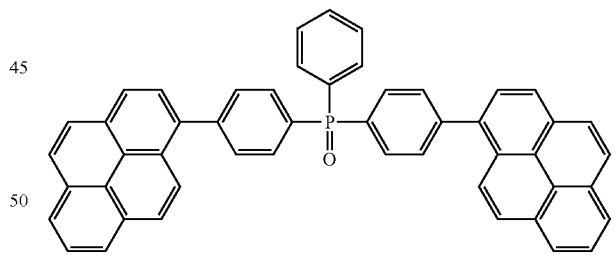

Figure 5:
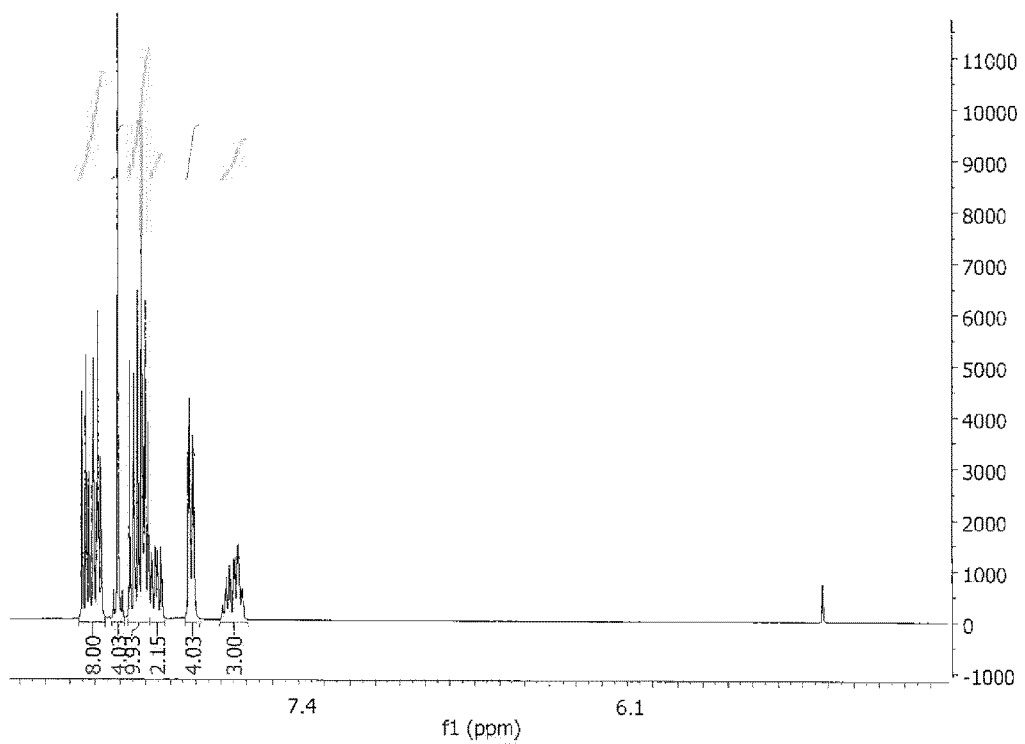
FIG. 5 shows $^1$H NMR spectrum of the inventive compound A3

According to general procedure B
bis(4-bromophenyl)(phenyl)phosphine oxide: 2.5 g (5.7 mmol, 1.0 eq)
1-pyreneboronic acid: 3.1 g (12.6 mmol, 2.2 eq)
Pd(PPh$_3$)$_4$: 265 mg (0.23 mmol, 4 mol. %)
K$_2$CO$_3$, 2M: 12 mL
DME: 30 mL
Column chromatography: $SiO_2$, ethyl acetate
Yield: 3.2 g yellow solid (82%)
mp: n.a. (glassy)
EI-MS: m/z=678
$^1$H-NMR: see FIG. 5 phenylbis(3-(pyren-1-yl)phenyl)phosphine oxide
(A4)

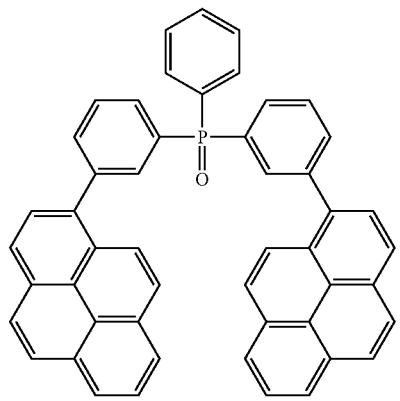 [SMILES: O=P(c1ccccc1)(c1cccc(-c2ccc3ccc4cccc5ccc2c3c45)c1)c1cccc(-c2ccc3ccc4cccc5ccc2c3c45)c1]

Figure 6:
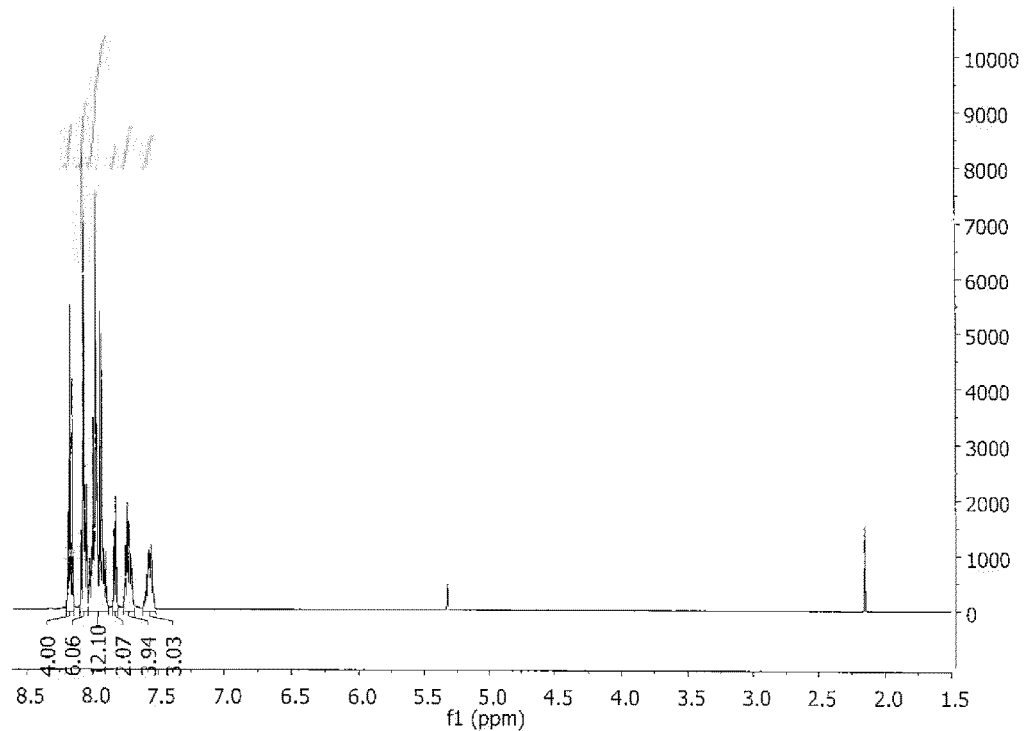
FIG. 6 shows $^1$H NMR spectrum of the inventive compound A4

According to general procedure B
bis(3-bromophenyl)(phenyl)phosphine oxide: 3.0 g (6.9 mmol, 1.0 eq)
1-pyreneboronic acid: 3.7 g (15.1 mmol, 2.2 eq)
Pd(PPh$_3$)$_4$: 318 mg (0.28 mmol, 4 mol. %)
K$_2$CO$_3$, 2M: 14 mL
DME: 35 mL
Column chromatography: SiO$_2$, ethyl acetate
Yield: 4.2 g yellow solid (90%)
mp: n.a. (glassy)
EI-MS: m/z=678
$^1$H-NMR: see FIG. 6

(4-(9,10-di(naphthalen-2-yl)anthracen-2-yl)phenyl)
diphenylphosphine oxide (B1)

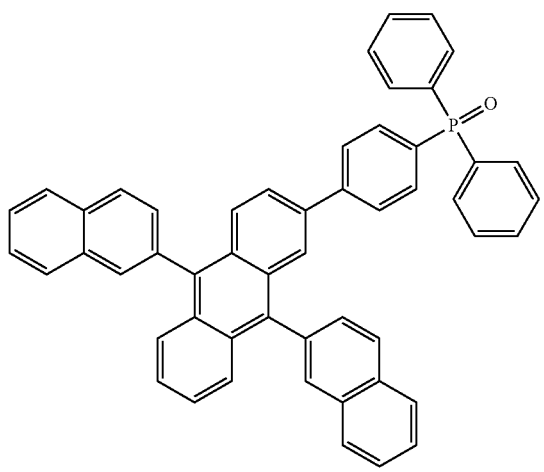 [SMILES: O=P(c1ccccc1)(c1ccccc1)c1ccc(-c2ccc3c(-c4ccc5ccccc5c4)c4ccccc4c(-c4ccc5ccccc5c4)c3c2)cc1]

Figure 7:
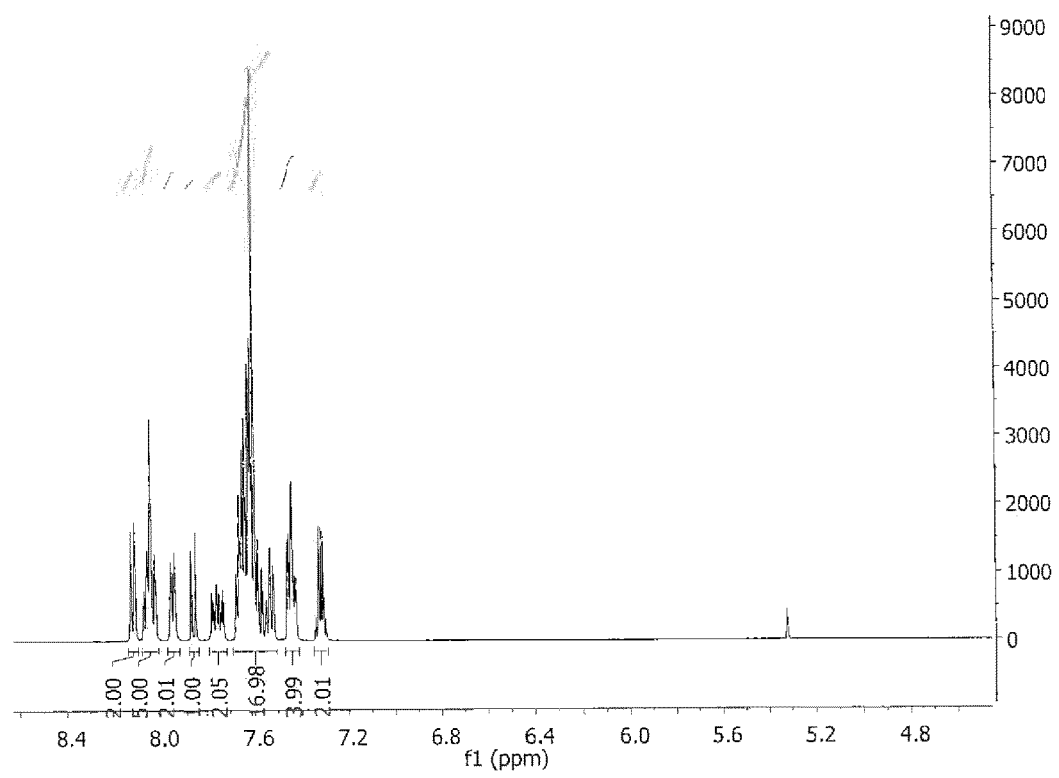
FIG. 7 shows $^1$H NMR spectrum of the inventive compound B1

According to general procedure B Known from WO02012/173370 (LG, paragraph 131) (4-bromophenyl)diphenylphosphine oxide: 1.88 g (5.3 mmol, 1.0 eq) (9,10-di(naphthalen-2-yl)anthracen-2-yl)boronic acid: 3.0 g (6.3 mmol, 1.2 eq)
Pd(PPh$_3$)$_4$: 183 mg (0.16 mmol, 3 mol. %)
K$_2$CO$_3$, 2M: 8 mL
DME: 20 mL
Column chromatography: SiO$_2$, ethyl acetate
Yield: 3.0 g (81%) yellow solid
mp: n.a. (glassy)
EI-MS: m/z=706
$^1$H-NMR: see FIG. 7

(3-(9,10-di(naphthalen-2-yl)anthracen-2-yl)phenyl)
diphenylphosphine oxide (B2)

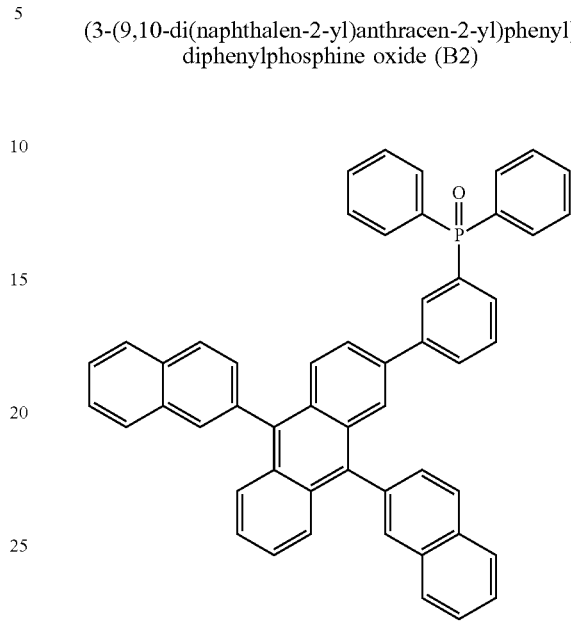

Figure 8:
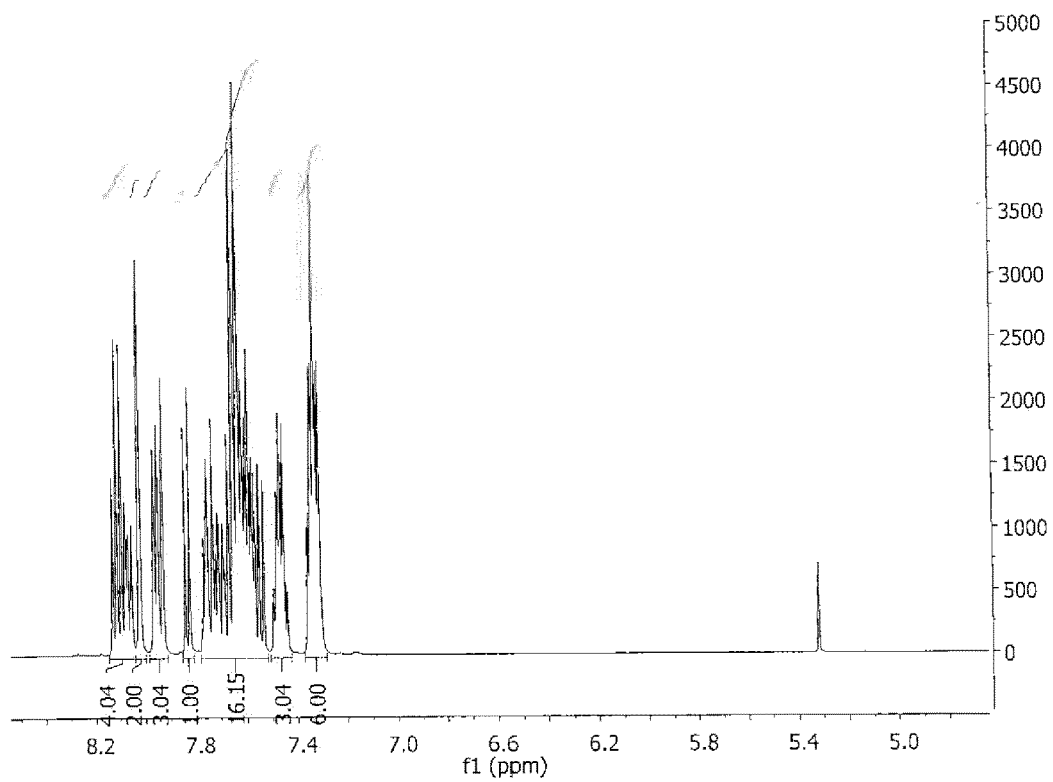
FIG. 8 shows $^1$H NMR spectrum of the inventive compound B2

According to general procedure B
(3-bromophenyl)diphenylphosphine oxide: 1.9 g (5.3 mmol, 1.0 eq)
(9,10-di(naphthalen-2-yl)anthracen-2-yl)boronic acid: 3.0 g (6.3 mmol, 1.2 eq)
Pd(PPh$_3$)$_4$: 183 mg (0.16 mmol, 3 mol. %)
K$_2$CO$_3$, 2M: 8 mL
DME: 20 mL
Column chromatography: SiO$_2$, ethyl acetate
Yield: 3.1 g (83%) yellow solid
mp: n.a. (glassy)
EI-MS: m/z=706
$^1$H-NMR: see FIG. 8

(9,10-di(naphthalen-2-yl)anthracen-2-yl)boronic acid

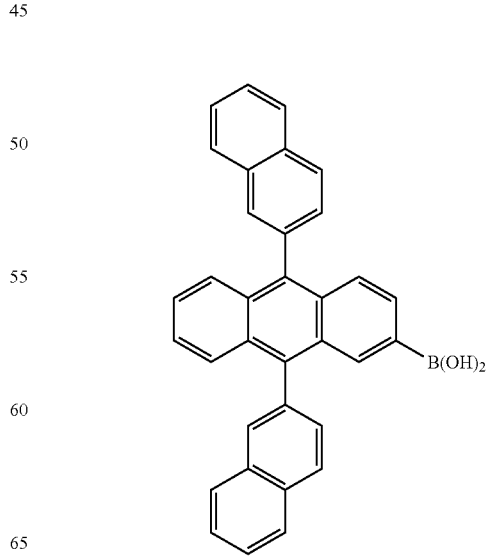

Prepared according to procedure described in EP13170862:

2-bromo-9,10-di(naphthalen-2-yl)anthracene (10.00 g, 1.0 eq, 19.63 mmol) was dissolved in THF (140 mL) and cooled to −78° C. At this temperature n-BuLi (2.5M in hexane, 10.2 mL, 1.3 eq, 25.52 mmol) was added dropwise and the mixture was stirred for 2 hours. Afterwards, B(OMe)$_3$ (6.12 g, 3.0 eq, 58.89 mmol) was added at −78° C. and the reaction mixture was allowed to warm up to room temperature. After stirring for 17 hours the mixture was quenched with HCl, the yellow precipitate was filtered off and washed with water (2×30 mL). The residue was dried in vacuo and used without further purification.

Yield: 9.8 g (100%)

diphenyl(pyren-1-yl)phosphine oxide (C1)

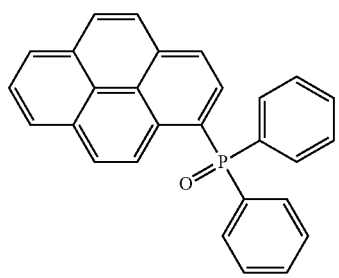 [SMILES: O=P(c1ccccc1)(c1ccccc1)c1ccc2ccc3cccc4ccc1c2c34]

Known (CAS 110988-94-8) for long, e.g. from JP 4 876 333 B2, commercially available.

(9,10-di(naphthalen-2-yl)anthracen-2-yl)diphenyl-phosphine oxide (C2)

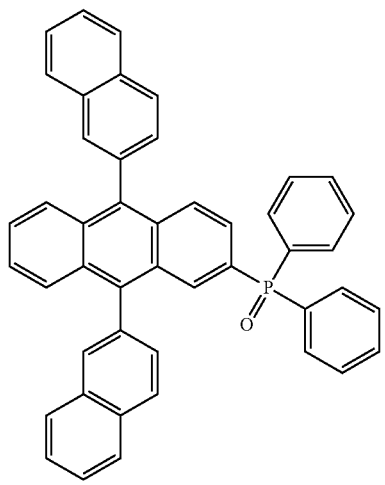 [SMILES: O=P(c1ccccc1)(c1ccccc1)c1ccc2c(-c3ccc4ccccc4c3)c3ccccc3c(-c3ccc4ccccc4c3)c2c1]

Synthesis according to general procedure A)
2-bromo-9,10-di(naphth-2-yl)-anthracene: 5.00 g (1.0 eq, 9.81 mmol)
n-butyl lithium, 2.5M in hexane: 4.7 mL (1.2 eq, 11.77 mmol)
THF: 50 mL
chlorodiphenylphosphine: 2.1 mL (1.2 eq, 11.77 mmol)
DCM: 60 mL
H$_2$O$_2$, 30 wt. % in water: 15 mL column chromatography (SiO$_2$, hexane:EE 1:1)
Yield: 3.20 g (52%)
Melting point: none (glassy compound)
ESI-MS: m/z=631 (M+H$^+$)

phenyldi(pyren-1-yl)phosphine oxide (C3)

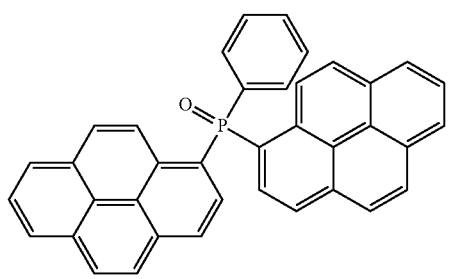 [SMILES: O=P(c1ccccc1)(c1ccc2ccc3cccc4ccc1c2c34)c1ccc2ccc3cccc4ccc1c2c34]

Known for long (CAS721969-93-3), commercially available, e.g. from Luminescence Technology Corp (TW).

Compounds A5-A7 and B3-B8 were synthesized by similar procedures as demonstrated above. T$_g$/mp (° C./° C.): B3 66/n.a. (glassy solid), B4 80/260, B5 114/290.7, B6 107/249.1, A6 96/225.7.

Dopants:

lithium quinolin-8-olate (D1)

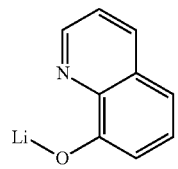

Commercially available lithium 2-(diphenylphosphoryl)phenolate (D2)

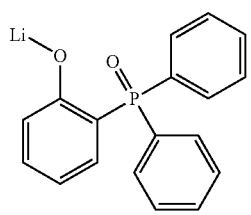

Synthesis according to patent application WO2013/079678 (compound (1), p. 15-16)

lithium 2-(diphenylphosphoryl)pyridin-3-olate (D3)

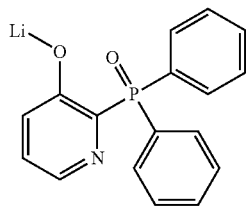

Synthesis according to patent application EP13170862:

1.1) diphenyl(pyridin-2-yl)phosphine oxide

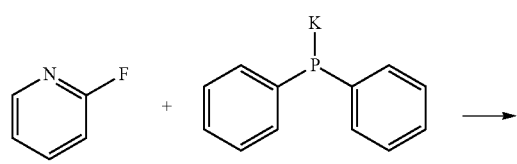

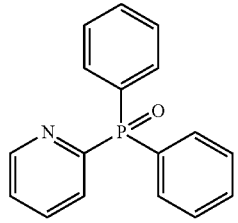

| 2-fluoropyridine | 2.50 g, 1.0 eq, 25.8 mmol |
|---|---|
| potassium diphenylphosphide | 51.5 mL, 1.0 eq, 25.8 mmol |
| THF | 50 mL |
| DCM | 80 mL |
| hydrogen peroxide, 30 wt. % in water | 25 mL |
| hexane | 20 mL |

Fluoropyridine was dissolved in dry THF. The potassium diphenylphosphide solution was added drop wise during one hour at room temperature. The resulting orange solution was stirred overnight at room temperature. The solvent was removed under reduced pressure and the residue dissolved in dichloromethane. Hydrogen peroxide was added slowly at 0° C. The mixture was stirred overnight at room temperature. The solvent was removed under reduced pressure and the residue treated with hexane. The resulting solid was filtered off, washed with hexane and dried in vacuum.

Yield: 2.2 g (31%), HPLC-MS purity 98.0%.

1.2) (3-hydroxypyridin-2-yl)diphenylphosphine oxide

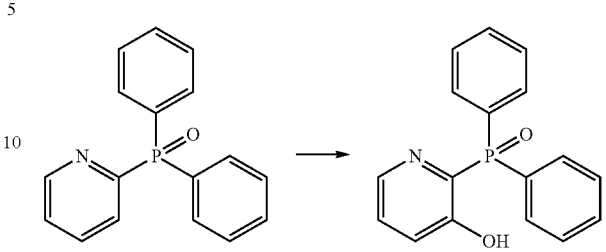

| diphenyl(pyridin-2-yl)phosphine oxide | 2.0 g, 1.0 eq., 7.2 mmol |
|---|---|
| 2-isopropoxy-4,4,5,5-tetramethyl-1,3,2-dioxaborolane | 4.35 mL, 3.0 eq., 21.5 mmol |
| lithium diisopropylamide (LDA) | 9.56 mL, 2.0 eq., 14.3 mmol |
| THF | 50 mL |
| Chloroform | 50 mL |
| hydrogen peroxide, 30 wt. % in water | 10 mL |
| DCM | 15 mL |

The starting material was dissolved in dry THF and cooled to −78° C. The borolane was added and the mixture stirred for 20 min. The LDA solution was added dropwise and the temperature was allowed to rise slowly to room temperature. The reaction was stirred for 3 days at room temperature. The solvent was removed under reduced pressure and the residue was dissolved in chloroform. Hydrogen peroxide was added slowly at 0° C. and the mixture was stirred overnight at room temperature. The mixture was extracted with chloroform and brine. The organic phase was dried over magnesium sulphate and the solvent removed under reduced pressure. The residue was dissolved in DCM and precipitated with hexane. The solid was filtered off, washed with hexane and dried in vacuum.

Yield: 1.4 g (67%), GCMS purity 100%, structure confirmed by $^1$H-NMR, $\square$ (ppm)=11.48 (s, 1H, OH), 8.25 (d X from ABX system, J=4.5 Hz, 1H), 7.90 (dd, J=12 Hz and 7.5 Hz, 4H), 7.58 (br t, J=7 Hz, 2H), 7.50 (td, J=7.5 Hz and 3 Hz, 4H), 7.30 (ddd, B from ABX system, 1H), 7.24 (br dd, A from ABX system, 1H).

1.3) lithium 2-(diphenylphosphoryl)pyridin-3-olate D3

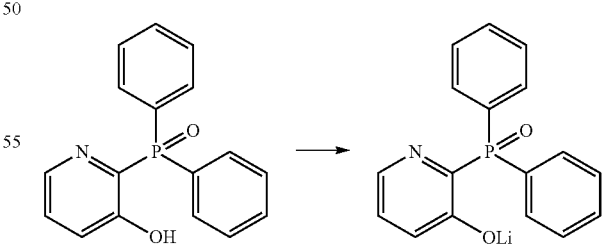

| (3-hydroxypyridin-2-yl)diphenylphosphine oxide | 1.0 g, 1.0 eq., 3.4 mmol |
|---|---|
| lithium tert-butoxide | 0.27 g, 1.0 eq., 3.4 mmol |
| acetonitrile | 40 mL |

The starting material was suspended in dry acetonitrile. Lithium tert-butoxide was added at room temperature and the mixture was heated at reflux for 13 hours. The solid was filtered off, washed with acetonitrile and dried in vacuum.

Yield: 0.865 g (87%), TGA-DSC: m.p. 442° C.

Analytical data (after sublimation):

TGA-DSC: mp 445° C.

Elemental analysis: 67.6% C-content (theor. 67.79%), 4.48% H-content (theor. 4.35%), 4.64% N-content (theor. 4.65%)

Device Examples

All data shown here are typical examples. The data in table 1 are medians over typically 16 identical diodes, which are described in the following examples.

Example 1

Bottom emission blue emitting OLED was made by depositing a 10 nm layer of N4,N4"-di(naphthalen-1-yl)-N4, N4"-diphenyl-[1,1':4',1"-terphenyl]-4,4"-diamine (HTM3) doped with 2,2',2"-(cyclopropane-1,2,3-triylidene)tris(2-(p-cyanotetrafluorophenyl)acetonitrile) (PD2, matrix to dopant weight ratio 92:8) onto a 90 nm thick ITO-glass substrate, followed by an 120 nm undoped layer of HTM3. Subsequently, a blue fluorescent emitting layer of ABH113 (Sun Fine Chemicals) doped with NUBD370 (Sun Fine Chemicals) (97:3 weight ratio) was deposited with a thickness of 20 nm. A 36 nm layer of the tested inventive or comparative compound was deposited on the emitting layer together with 50 wt. % D1 or D2 as ETL. Subsequently a layer of aluminium with a thickness of 100 nm was deposited.

The observed voltages and quantum efficiencies at the current density 10 mA/cm$^2$ are reported in the Table 1.

FIG. 9 and FIG. 10 depict OLED performance curves of devices comprising as electron transporting matrices compounds B2 or C2, respectively. Both compounds comprise the same 9,10-bis(2-naphtyl)-2-anthryl electron transporting unit E. B2 and C2 were tested as representative examples for anthracene based electron transport materials. One can see the combination of the inventive compound B2 and dopant D2 is superior to C2 either doped with D1 or D2 as it provides lower voltage and higher efficiency resulting in an overall advantage represented by the second highest power efficiency reported in table 1. This indicates clearly an unexpected beneficial effect for compounds, which have a phenylene spacer introduced between the P=O group and the electron transporting unit, in combination with the dopant D2. On top, table 1 visualizes that also B1 is superior to C2, being indicative for the generality of the inventive compound building principle. One has to highlight, that in this case the meta-phenylene performance (B2) is better than the para-phenylene performance (B1).

FIG. 11 and FIG. 12 depict OLED performance curves of devices comprising as electron transporting matrices compounds A4 or C3, respectively. Both compounds comprise two 1-pyrenyl electron transporting units E. One can see the combination of the inventive compound A4 and dopant D2 is superior to C3 either doped with D1 or D2 with respected to efficiency, while only paying a small penalty in voltage. The power efficiency (table 1) relativizes both values and reveals that A4 with D2 is the best performing combination described.

Example 2

Top emission blue emitting OLED was made by depositing a 10 nm layer of HTM3 doped with PD2 (matrix to dopant weight ratio 92:8) onto a 100 nm thick Ag anode deposited on a glass substrate, followed by an 120 nm undoped layer of HTM3. Subsequently, a blue fluorescent emitting layer of ABH113 (Sun Fine Chemicals) doped with NUBD370 (Sun Fine Chemicals) (97:3 wt %) was deposited with a thickness of 20 nm. A 36 nm layer of the tested inventive or comparative compound was deposited on the emitting layer together with 50 wt. % D1 or D2 as ETL. Subsequently, a 12 nm layer of magnesium doped silver (10 vol. % Mg) was used as transparent cathode top contact.

The observed voltages are reported at 10 mA/cm$^2$ and current efficiencies are determined at the luminances of 1000 Cd/m$^2$ for examples reported in the Table 1.

That top-emission device structure was chosen to demonstrate independency of the performance of the inventive compounds from the OLED structure. A1 and C1 were chosen as examples for mono-pyrene based electron transport materials.

FIG. 13 and FIG. 14 depict OLED performance curves of top emitting OLEDs according to Example 2 comprising as electron transporting matrices compounds B2 or C2, respectively. Both compounds comprise the same 1-pyrenyl electron transporting unit E. One can see that the combination of the inventive compound A1 and dopant D2 is superior to C1 with respect to efficiency either doped with D1 or D2. It is remarkable that no penalty in voltage is paid, also resulting in significantly higher power efficiencies. Again, it can be shown that even in top emission structures, the unexpected beneficial effect for compounds containing a phenylene spacer introduced between the P=O group and the electron transporting unit can be observed in D2 doped semiconducting materials.

FIG. 15 shows the emission spectra for the above discussed OLEDs, proving very good comparability of devices comprising tested electron transporting materials as regards colour of the emitted light.

When comparing all data in the Table 1, it becomes clear that the advantageous effect of the introduction of an phenylene spacer unit between P=O and electron transport unit is more pronounced in case of D2 doping rather than D1 doping, showing the inventiveness of the electron transporting materials comprising matrix compound of formula (I) in combination with a compound of formula (II).

As regards structure-activity relationships in inventive matrix compounds of formula (I), the comparison of power efficiencies in devices comprising para-compounds (A1, A3, B1) vs. meta-compounds (A2, A4, B2) shows that meta-substitution pattern in the phenylene spacer is favourable. Nonetheless, the para-phenylene compounds still in average outperform the compounds that do not contain a phenylene-spacer unit at all.

All the data underline the unexpected beneficial effect of introducing a phenylene spacer unit into known triaryl phosphine oxide electron transport materials, especially if the spacer comprising compound is used with compound of formula (II) as n-dopant.

The features disclosed in the foregoing description, in the claims and in the accompanying drawings may both separately and in any combination be material for realizing the invention in diverse forms thereof.

Used Acronyms and Abbreviations

CGL charge generating layer

CV cyclovoltammetry

DCM dichloromethane

DSC differential scanning calorimetry

DFT density functional theory

DME 1,2-dimethoxyethane

EA electron affinity
EE ethylester (ethyl acetate)
EI electron impact (direct inlet mass spectroscopy)
EIL electron injection layer
ESI electrospray ionization (mass spectroscopy)
ETL electron transporting layer
ETM electron transporting matrix
Fc$^+$/Fc ferrocenium/ferrocene reference system
GC gas chromatography
HIL hole injection layer
HPLC high performance liquid chromatography
HOMO highest occupied molecular orbital
HTL hole transporting layer
HTM hole transporting matrix
IP ionisation potential
IPES inverted photoelectron spectroscopy
ITO indium tin oxide
LDA lithium diisopropyl amide
LUMO lowest unoccupied molecular orbital
MS mass spectroscopy
NMR nuclear magnetic resonance
OLED organic light emitting diode
RT room temperature
SPS solvent purification system
TGA thermogravimetry thermal analysis
THF tetrahydrofuran
TLC thin layer chromatography
UPS ultraviolet photoelectron spectroscopy
UV spectroscopy in the ultra violet/visible range of light spectrum
VTE vacuum thermal evaporation
eq chemical equivalent
mol. % molar percent
vol. % volume percent
wt. % weight (mass) percent
mp melting point
n.a. not applicable

The invention claimed is:

1. A semiconducting material comprising:
i) a compound according to formula (I)

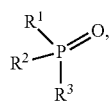

(I)

wherein $R^1$, $R^2$, and $R^3$ are independently selected from $C_1$-$C_{30}$-alkyl, $C_3$-$C_{30}$ cycloalkyl, $C_2$-$C_{30}$-heteroalkyl, $C_6$-$C_{30}$-aryl, $C_2$-$C_{30}$-heteroaryl, $C_1$-$C_{30}$-alkoxy, $C_3$-$C_{30}$-cycloalkyloxy, $C_6$-$C_{30}$-aryloxy, or a structural unit having general formula E-A-,
wherein
A is a phenylene spacer unit, and
E is an electron transporting unit selected from $C_{10}$-$C_{60}$ aryl or $C_6$-$C_{60}$ heteroaryl, wherein the $C_6$-$C_{60}$ heteroaryl comprises from 1 to 6 heteroatoms independently selected from O, S, P, Si, or B, and the $C_{10}$-$C_{60}$ aryl or $C_6$-$C_{60}$ heteroaryl comprises a conjugated system of at least 10 delocalized electrons, and
wherein at least one of $R^1$, $R^2$, and $R^3$ has the general formula E-A-;
and
ii) at least one lithium complex having formula (II)

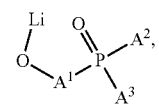

(II)

wherein $A^1$ is a $C_6$-$C_{30}$ arylene or $C_2$-$C_{30}$ heteroarylene comprising at least one atom selected from O, S, or N in an aromatic ring, and each of $A^2$ and $A^3$ is independently selected from $C_6$-$C_{30}$ aryl or $C_2$-$C_{30}$ heteroaryl comprising at least one atom selected from O, S, or N in an aromatic ring.

2. The semiconducting material according to claim 1, wherein in the compound of formula (I), spacer A is selected from m- or p-phenylene.

3. The semiconducting material according to claim 1, wherein in the compound of formula (I), electron transporting unit E is a $C_{14}$-$C_{50}$ aryl or a $C_8$-$C_{50}$ heteroaryl.

4. The semiconducting material according to claim 3, wherein in the compound of formula (I), electron transporting unit E is a $C_{14}$-$C_{44}$ aryl.

5. The semiconducting material according to claim 4, wherein in the compound of formula (I), at least one group E is selected from $C_{16}$-$C_{44}$ pyrenyl or $C_{14}$-$C_{38}$ anthryl.

6. The semiconducting material according to claim 4, wherein in the compound of formula (I), in at least one electron transporting unit E-A-,
i) A is m- or p- phenylene, and E is $C_{16}$-$C_{44}$ pyrenyl; or
ii) A is m-phenylene, and E is $C_{14}$-$C_{34}$ anthryl.

7. The semiconducting material according to claim 1, wherein in the compound of formula (I), at least one of substituents $R^1$, $R^2$, and $R_3$ is phenyl.

8. The semiconducting material according to claim 1, wherein in the compound of formula (II), $A^1$ is phenylene.

9. The semiconducting material according to claim 1, wherein in the compound of formula (II), at least one of substituents $A^2$ and $A^3$ is phenyl.

10. An electronic device comprising a cathode, an anode and the semiconducting material according to claim 1, wherein the semiconducting material is arranged between the cathode and the anode.

11. The electronic device according to claim 10, further comprising an electron transporting layer or an electron injecting layer, wherein the semiconducting material is present in the electron transporting layer or the electron injecting layer.

12. The electronic device according to claim 11, wherein the electronic device is a light emitting device.

13. A compound having a structure according to formula (I):

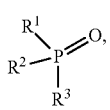

(I)

wherein $R^1$, $R^2$, and $R^3$ are independently selected from $C_1$-$C_{30}$-alkyl, $C_3$-$C_{30}$-cycloalkyl, $C_2$-$C_{30}$-heteroalkyl, $C_6$-$C_{30}$-aryl, $C_2$-$C_{30}$-heteroaryl, $C_1$-$C_{30}$-alkoxy, $C_3$-$C_{30}$-cycloalkyloxy, $C_6$-$C_{30}$-aryloxy, or a structural unit having general formula E-A-, wherein at least one group selected from $R^1$, $R^2$, or $R^3$ has the general formula E-A-,
wherein
A is m-phenylene, and
each E is an electron transporting unit independently selected from $C_{14}$-$C_{60}$ aryl or $C_6$-$C_{60}$ heteroaryl, wherein the $C_6$-$C_{60}$ heteroaryl comprises from 1 to 6 heteroatoms independently selected from O, S, P, Si, or B, and the $C_{14}$-$C_{60}$ aryl or $C_6$-$C_{60}$ heteroaryl comprises a conjugated system of at least 10 delocalized electrons.

14. A compound having a structure according to formula (I):

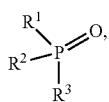

wherein $R^1$, $R^2$, and $R^3$ are independently selected from $C_1$-$C_{30}$-alkyl, $C_3$-$C_{30}$-cycloalkyl, $C_2$-$C_{30}$-heteroalkyl, $C_6$-$C_{30}$-aryl, $C_2$-$C_{30}$-heteroaryl, $C_1$-$C_{30}$-alkoxy, $C_3$-$C_{30}$-cycloalkyloxy, $C_6$-$C_{30}$-aryloxy, or a structural unit having general formula E-A-,
wherein at least one group selected from $R^1$, $R^2$, or $R^3$ has the general formula E-A-,
wherein
i) A is m- or p-phenylene, and E is $C_{16}$- $C_{44}$ pyrenyl; or
ii) A is m-phenylene, and E is $C_{14}$- $C_{38}$ anthryl.

15. A compound having a structure according to formula (I):

wherein $R^1$, $R^2$, and $R^3$ are independently selected from $C_1$-$C_{30}$-alkyl, $C_3$-$C_{30}$-cycloalkyl, $C_2$-$C_{30}$-heteroalkyl, $C_6$-$C_{30}$-aryl, $C_2$-$C_{30}$-heteroaryl, $C_1$-$C_{30}$-alkoxy, $C_3$-$C_{30}$-cycloalkyloxy, $C_6$-$C_{30}$-aryloxy, or a structural unit having general formula E-A-,
wherein at least one group selected from $R^1$, $R^2$, or $R^3$ has the general formula E-A-,
wherein
A is o-phenylene, and
each E is an electron transporting unit independently selected from $C_{14}$-$C_{60}$ aryl or $C_6$-$C_{60}$ heteroaryl, wherein the $C_6$-$C_{60}$ heteroaryl comprises from 1 to 6 heteroatoms independently selected from O, S, P, Si, or B, and the $C_{14}$-$C_{60}$ aryl or $C_6$-$C_{60}$ heteroaryl comprises a conjugated system of at least 10 delocalized electrons.

* * * * *